(12) United States Patent
Jansen et al.

(10) Patent No.: US 8,647,257 B2
(45) Date of Patent: Feb. 11, 2014

(54) CANNULOTOME

(76) Inventors: Lex P. Jansen, Pleasanton, CA (US);
John T. To, Newark, CA (US); John W. Davis, Sunnyvale, CA (US); Stewart M. Kume, Emerald Hills, CA (US); Wendy Twardzik, New York, NY (US)

( * ) Notice: Subject to any disclaimer, the term of this patent is extended or adjusted under 35 U.S.C. 154(b) by 0 days.

(21) Appl. No.: 13/245,826

(22) Filed: Sep. 26, 2011

(65) Prior Publication Data

US 2012/0016192 A1 Jan. 19, 2012

Related U.S. Application Data

(63) Continuation of application No. 13/237,866, filed on Sep. 20, 2011.

(60) Provisional application No. 61/384,463, filed on Sep. 20, 2010.

(51) Int. Cl.
*A61B 1/00* (2006.01)

(52) U.S. Cl.
USPC ............ 600/104; 600/114; 606/167; 606/185

(58) Field of Classification Search
USPC .................. 600/114, 127, 129; 606/184–185
See application file for complete search history.

(56) References Cited

U.S. PATENT DOCUMENTS

| | | | |
|---|---|---|---|
| 4,573,448 A | 3/1986 | Kambin | |
| 5,306,245 A | 4/1994 | Heaven | |
| 5,406,940 A | 4/1995 | Melzer et al. | |
| 5,445,142 A * | 8/1995 | Hassler, Jr. | 600/105 |
| 5,448,990 A * | 9/1995 | De Faria-Correa | 600/129 |
| 5,674,184 A | 10/1997 | Hassler, Jr. | |
| 5,681,262 A * | 10/1997 | Isse | 600/127 |
| 5,685,879 A | 11/1997 | Phillips | |
| 5,820,546 A | 10/1998 | Ouchi | |
| 6,039,748 A * | 3/2000 | Savage et al. | 606/180 |
| 6,099,464 A | 8/2000 | Shimizu et al. | |
| 6,217,509 B1 | 4/2001 | Foley et al. | |
| 6,387,043 B1 * | 5/2002 | Yoon | 600/109 |
| 6,394,949 B1 * | 5/2002 | Crowley et al. | 600/127 |
| 6,453,044 B1 * | 9/2002 | Klitzner et al. | 379/430 |
| 6,752,755 B2 * | 6/2004 | Akiba | 600/127 |
| 6,770,026 B2 * | 8/2004 | Kan et al. | 600/114 |
| 7,060,024 B2 | 6/2006 | Long et al. | |
| 7,108,705 B2 | 9/2006 | Davison et al. | |
| 7,273,468 B2 | 9/2007 | Bedell | |
| 7,485,092 B1 * | 2/2009 | Stewart et al. | 600/127 |
| 8,246,535 B2 | 8/2012 | Sutoh | |
| 2007/0225564 A1 * | 9/2007 | Couvillon et al. | 600/140 |
| 2007/0260273 A1 * | 11/2007 | Cropper et al. | 606/185 |
| 2009/0281386 A1 | 11/2009 | Acosta et al. | |
| 2010/0121153 A1 | 5/2010 | To | |
| 2011/0184234 A1 | 7/2011 | Lopez et al. | |

FOREIGN PATENT DOCUMENTS

WO 2008064842 A2 6/2008

* cited by examiner

*Primary Examiner* — Matthew J Kasztejna
(74) *Attorney, Agent, or Firm* — Ross M. Carothers; Morrison & Foerster LLP

(57) ABSTRACT

Systems and methods for treating spinal stenosis include endoscopic access devices and bone removal devices used to perform a foraminotomy or other bone removal procedures. A bone removal device includes a cannulotome with an endoscopic imaging lumen. Optionally, an endoscope retaining device can be used to facilitate advancement of the endoscope through the cannulotome.

22 Claims, 30 Drawing Sheets

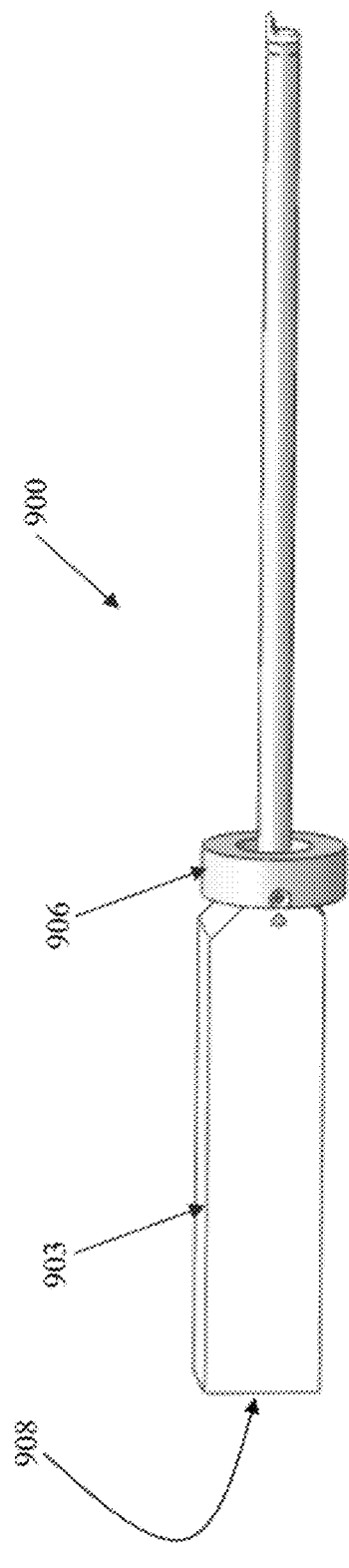
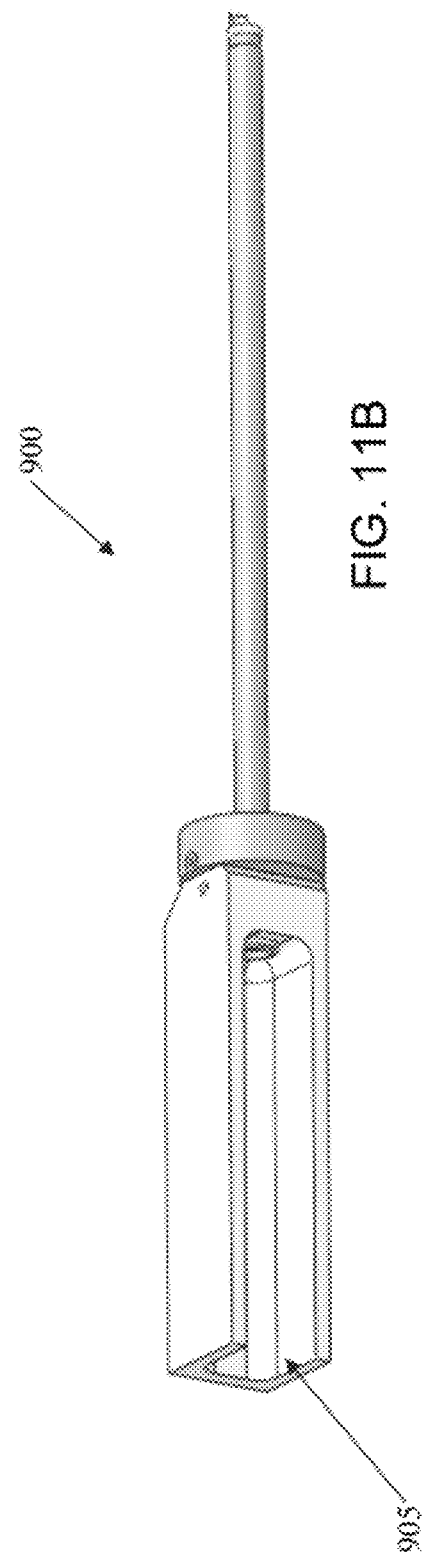

CANNULOTOME

RELATED APPLICATIONS

This application is a continuation of U.S. patent application Ser. No. 13/237,866, filed Sep. 20, 2011, which claims benefit from U.S. Provisional Application Ser. No. 61/384,463, filed Sep. 20, 2010, the disclosures of which are hereby incorporated by reference in their entirety.

BACKGROUND

Spinal stenosis is a disorder where narrowing occurs in the spaces of the spine. The disorder may affect the central canal of the spine in which the spinal cord is housed (e.g. central spinal stenosis) or the lateral foramina formed between two adjacent vertebrae from which the spinal nerves exit (e.g. lateral spinal stenosis). Spinal stenosis is frequently associated with degenerative disease of vertebral disc and/or vertebrae. The degenerative changes may cause reactive bony or ligament ingrowth and may reduce vertebral spacing, which may lead to nerve impingement. This nerve impingement may result in debilitating forms of sciatica, which is a radiating pain to limbs or upper body and further areas in the body, as well as limitations in physical movement due to this pain.

Temporary relief of pain of this condition is often sought through conservative therapy, which includes positional therapy (e.g. sitting or bending forward to reduce pressure on spine), physical therapy, and medication or drug therapy to reduce pain and inflammation. When conservative therapy fails to resolve a patient's symptoms, surgery may be considered to address the structural etiologies of the symptoms. Surgical treatments for suspected spinal stenosis often involve open procedures that require extensive dissection of muscle, connective tissue and bone along a patient's back to achieve adequate surgical exposure. These surgeries also expose the patient to a significant risk of complications, due to the presence of critical neurovascular structures near the surgical site. Specific surgical treatments include 1) foraminotomy, which involves the removal of bone surrounding an impinged nerve, 2) laminectomy, where the arch-like bone forming the posterior border of the spinal canal is removed to relieve pressure on the nerve roots or spinal cord, 3) discectomy, which involves removal of vertebral disc material impinging on a nerve, and 4) spinal fusion, which involves the use of grafts or implants to stabilize the movement between two vertebrae by eliminating any relative motion between them.

BRIEF SUMMARY

Systems and methods for treating spinal stenosis include endoscopic access devices and bone removal devices used to perform a foraminotomy or other bone removal procedures. A bone removal device includes a cannulotome with an endoscopic imaging lumen. Optionally, an endoscope retaining device can be used to facilitate advancement of the endoscope through the cannulotome.

Described herein is a system for spinal surgery that may comprise a tissue removal device comprising a proximal handle, an elongate shaft with a lumen terminating at a distal opening comprising a perimeter with a tapered protrusion, and an endoscope retaining device comprising an elongate support structure configured to receive an endoscope. The tapered protrusion may comprise a proximal base and a distal cutting edge and at least one-quarter of the perimeter lies at or proximal to the base. The endoscope retaining device may be configured to be coupled to the proximal handle of the tissue removal device in a predetermined radial orientation. In some variations, the cutting edge may comprise a notch, such that the proximal-most portion of the notch is distal to the proximal base of the tapered protrusion. The tapered protrusion may comprise an exterior surface and an interior surface that converge at the cutting edge. The taper angle between the exterior and interior surface may be 20° or less, or 10° or less. In some variations, the exterior surface of the tapered protrusion may comprise one or more recesses configured to retain a therapeutic substance. The one or more recesses have a circular shape or rectangular shape, and the therapeutic agent may be bone wax. In some variations, the interior surface of the tapered protrusion may comprise one or more orientation markings.

Some variations of systems for spinal surgery may also comprise an endoscope configured to be coupled to the endoscope retaining device. Optionally, the system may further comprise a cannula, where the tissue removal device is configured to extend through the cannula. In some variations, the tissue removal device is configured to extend through a retractor cannula comprising one or two distal jaws.

An endoscope retaining device for spinal surgery may further comprise a proximal handle attached to a proximal portion of the elongate support structure, and a distal securing element. The distal securing element may be configured to partially enclose a distal circumferential surface of an endoscope in a predetermined rotational alignment, while partially exposing the distal circumferential surface. In some variations, the endoscope retaining device may further comprise an outer sheath, wherein the support structure is at least partially enclosed within the outer sheath. The elongate support structure may comprise one or more tubular channels configured to transport fluid along the support structure, and each tubular channel may comprise an external surface and an internal surface. In some variations, a distal securing structure may comprise one or more retention tabs configured to engage the distal portion of an endoscope. The support structure may comprise a longitudinal slot configured to axially provide a predetermined range of relative longitudinal movement between an endoscope and the support structure. Some variations of a support structure may further comprise an arched protruding structure that extends along a longitudinal length of the support structure. The arched structure may be configured to position the support structure within the lumen of the cannulotome shaft. In some variations, a distal portion of the support structure may comprise a bend region. The bend region may have a first stressed straight configuration and a second relaxed bent configuration. The system may comprise a mandrel insertable through the endoscope retaining device and along the support structure. In the first straight configuration, the mandrel is in a position distal to the bend region, and in the second bent configuration, the mandrel is in a position proximal to the bend region. Alternatively or additionally, a system for spinal surgery may further comprise a grasper tool insertable through the endoscope retaining device and along the support structure.

In some variations, the tissue removal device handle may comprise a slot and the endoscope retaining device handle may comprise one or more flanges, where the tissue removal device handle is configured to retain the endoscope retaining device handle such that the flanges are aligned along the slot. In some variations, the tissue removal device handle may be configured to retain the endoscope retaining device by friction-fit. Alternatively or additionally, the endoscope retaining device handle may be configured to engage an endoscope using a latch mechanism. A system for spinal surgery may also comprise an endoscope attachment tab configured to releasably engage with a length of an endoscope cable, such that the endoscope retaining device handle is configured to engage the endoscope attachment tab. In some variations, the endoscope retaining device handle is configured to engage an endoscope using a spring-based mechanism. A grasping device may also be included in some variations, where the grasping device is configured to be inserted through the outer sheath of the endoscope retaining device.

Also described herein is one example of an endoscope stabilization system comprising an endoscope and an endoscope retaining device comprising a proximal handle and an elongate support structure attached to the handle. The support structure may comprise an elongate structure with retention protrusions configured to releasably secure a distal portion of the endoscope. The support structure may also comprise one or more tubular structures along a side of the elongate structure configured for transporting fluid along the endoscope retaining device. In some variations, the endoscope retaining device further comprises a tube that is attached to the proximal handle, where the support structure is at least partially enclosed in a lumen of the tube. The endoscope retaining device may be configured to retain the endoscope such that the endoscope is axially aligned with the support structure. For example, the endoscope retaining device and the endoscope may comprise corresponding structures such that alignment of the corresponding structures axially aligns the endoscope with the support structure. In one variation, the endoscope comprises a protrusion and the elongate structure comprises a longitudinal slot such that insertion of the protrusion within the slot axially aligns the protrusions with the support structure. In some variations, the distal portion of the support structure may also comprise an arched protruding structure that extends along a longitudinal length of the support structure, the arched structure configured to position the support structure within the lumen the tube. In some variations, a distal portion of the support structure structure comprises a bend region, wherein the bend region has a first stressed straight configuration and second relaxed bent configuration. The system may comprise a mandrel insertable through the endoscope retaining device and along the support structure. In the first straight configuration, the mandrel is in a position distal to the bend region, and in the second bent configuration, the mandrel is in a position proximal to the bend region. Alternatively or additionally, a system for spinal surgery may further comprise a grasper tool insertable through the endoscope retaining device and along the support structure.

In some variations of endoscope retaining devices, the support structure comprises two or more proximal tabs, where the proximal tabs correspond to two or more recesses in the proximal handle of the endoscope retaining device. The support structure may be engaged to the proximal handle of the endoscope retaining device by engaging the proximal tabs within the recesses. Alternatively or additionally, the proximal handle may be configured to engage the endoscope using a latch mechanism. In some variations, an endoscope stabilization system may comprise an endoscope attachment tab configured to releasably engage with a length of an endoscope cable, where the proximal handle is configured to engage the endoscope attachment tab. Additionally or alternatively, the endoscope retaining device handle may be configured to engage the endoscope using a spring-based mechanism. Optionally, an endoscope stabilization system may also comprise an introducer cannula.

Also described herein are methods for spinal surgery. One variation of a method for spinal surgery may comprise inserting an introducer cannula into a target spine region, advancing an endoscope assembly comprising an endoscope coupled to an endoscope retaining device through the lumen of the introducer cannula, wherein the endo scope retaining device comprises a channel therethrough, withdrawing the endoscope assembly, advancing a cannulotome with a proximal handle, an elongate shaft with a lumen therethrough, and a tapered cutter at the distal end of the shaft through the lumen of the introducer cannula, applying force to the cannulotome to remove bony or calcified tissue while simultaneously visualizing the removal of the tissue through a lumen of the cannulotome, drawing the tissue up through the lumen of the cannulotome shaft, and withdrawing the cannulotome. In some variations, the method may further comprise infusing fluid through the channel of the endoscope retaining device to the target spine region. The method may also comprise advancing the endoscope assembly through the cannulotome shaft lumen. Optionally, the method may comprise lubricating the lumen of the introducer cannula. In some variations, applying force to the cannulotome comprises tapping the cannulotome handle with a mallet.

Another variations of a method for spinal surgery may comprise inserting a cannulotome with a proximal handle, an elongate shaft with a lumen therethrough, and a tapered cutter at the distal end of the shaft through an introducer cannula, advancing an endoscope assembly comprising an endoscope coupled to an endoscope retaining device through the lumen of the cannulotome, wherein the endoscope retaining device comprises a channel therethrough, advancing the introducer cannula to a target spine region, and applying force to the cannulotome to remove bony or calcified tissue while simultaneously visualizing the removal of the tissue through a lumen of the cannulotome. In some variations, the method may further comprise infusing fluid through the channel of the endoscope retaining device to the target spine region. In some variations, the distal cutter of the cannulotome may comprise orientation markings, such that advancing the endoscope assembly comprises positioning the endoscope assembly according to the orientation markings. Applying force to the cannulotome may comprise tapping the cannulotome handle with a mallet. In some variations, endoscope images may be acquired during or immediately after the application of force to the cannulotome. Methods may further comprise rotating the cannulotome within the introducer cannula to contact a different tissue region. In some variations, the method may comprise drawing up the removed tissue through the cannulotome shaft lumen using a grasping tool. Optionally, some variations of a method for spinal surgery further comprise discarding the endoscope retaining device at the end of the procedure.

BRIEF DESCRIPTION OF THE DRAWINGS

FIGS. 11A and 11B are superior and inferior views of the cannulotome device in FIG. 36, without the endoscope.

DETAILED DESCRIPTION

Medication and physical therapy may be considered temporary solutions for spine-related disorders. These therapies, however, may not fully address the underlying pathologies. In contrast, current surgical solutions such as laminectomy, where the laminae (thin bony plates covering the spinal canal) are removed, permit exposure and access to the nerve root which does address the underlying pathologies. From there, bone fragments impinging the nerves may be removed. Screws, interbody spacers, and fixation plates may also be used to fuse or stabilize the spine following laminectomy. These surgical techniques, however, are quite invasive and require extensive preparation and prolonged exposure time during the surgery, often prolonging an already significant recovery time. Removal of bone tissue in close proximity to nerves may also increase the risk of neurovascular damage. Other surgical methods have been attempted, such as laminotomy, which focuses on removing only certain portions or smaller segments of the laminae. Although removing less bone may be less invasive, risks of iatrogenic blood vessel and nerve damage may increase. Some spine procedures also utilize posterior approaches to the spine, which may require deliberate removal of an intervening spinous process merely to achieve access to the desired surgical site.

To be the least destructive to spine structures while preserving the strength of the bones, a spinal procedure may be minimally invasive while also reducing the amount of excised, native bone or dissection of surrounding native tissues. The exemplary embodiments described herein include but are not limited to minimally invasive access systems and methods for performing foraminotomy, and tools for removing bone while preserving the adjacent soft tissue such as nerves and blood vessels.

Figure 1:
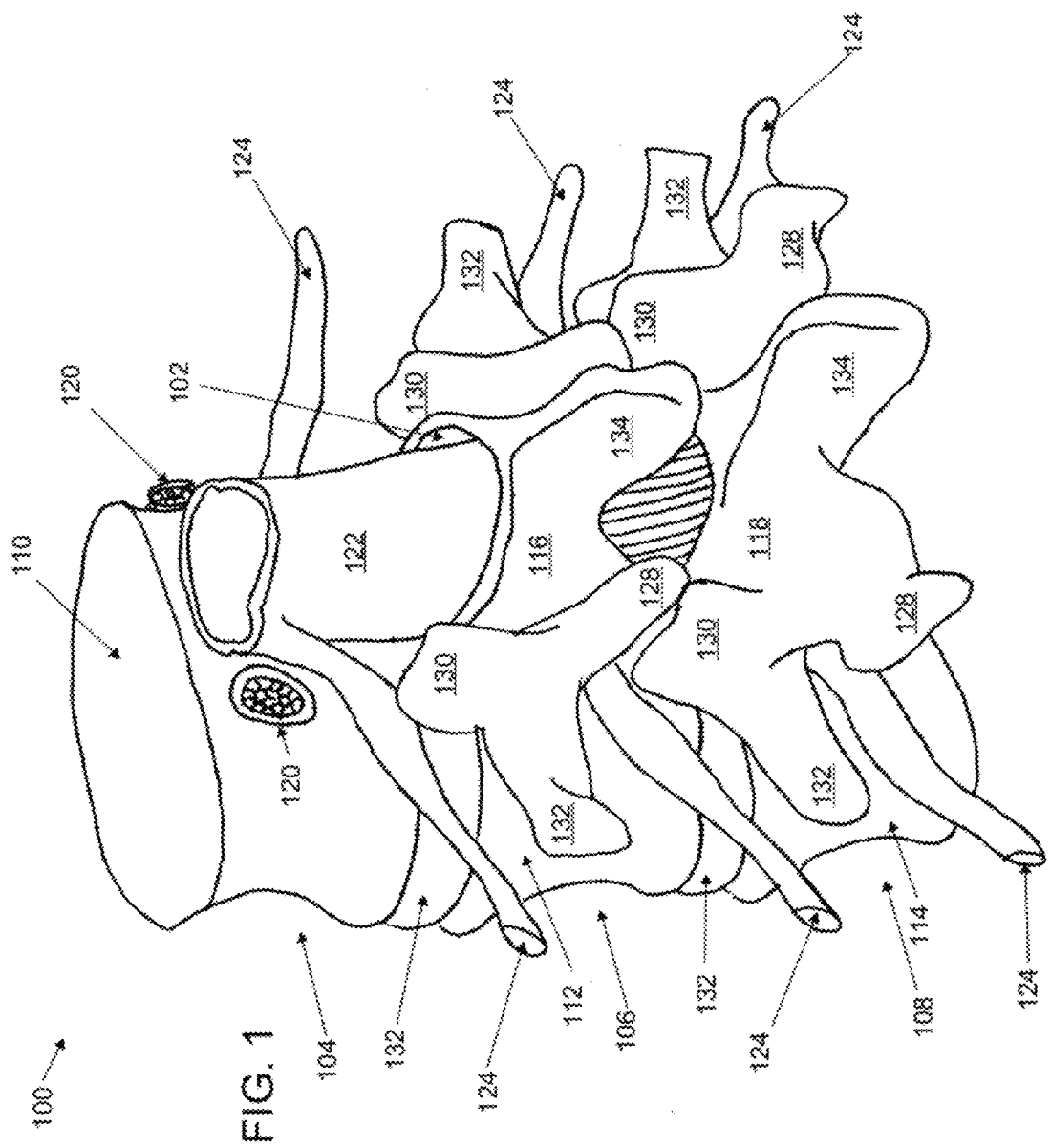
FIG. 1 is a schematic perspective view of a portion of a lumbar spine.

FIG. 1 is a schematic perspective view of a lumbar portion of a spine 100. The vertebral canal 102 is formed by a plurality of vertebrae 104, 106, and 108, which comprise vertebral bodies 110, 112, and 114 anteriorly and vertebral arches 116 and 118 posteriorly. The vertebral arch and adjacent connective tissue of the superior vertebra 104 in FIG. 1 has been omitted to better illustrate the spinal cord 122 within the vertebral canal 102. Spinal nerves 124 branch from the spinal cord 122 bilaterally and exit the vertebral canal 102 through intervertebral foramina 126 that are formed between adjacent vertebra 104, 106 and 108. The intervertebral foramina 126 (depicted in FIG. 2) are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are vertebral discs 132.

Figure 2:
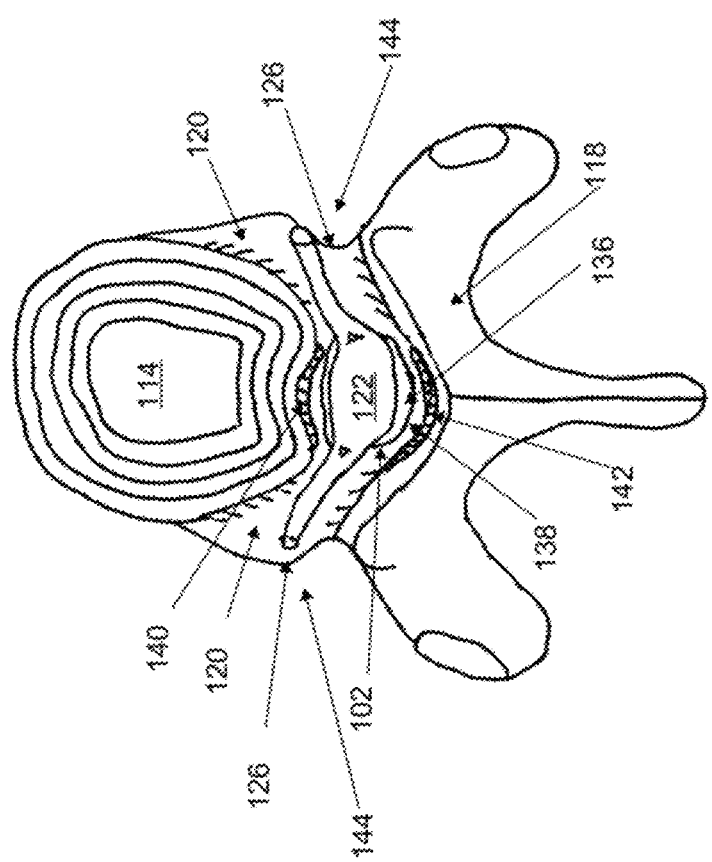
FIG. 2 is a schematic superior view of a portion of a lumbar vertebra and disc.

Referring to FIG. 2, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142, respectively, of the vertebral canal 102, and laterally by the pedicles 120 of the vertebral arches 116 and 118 and the intervertebral foramina 126. The epidural space 138 is contiguous with the paravertebral space 144 via the intervertebral foramina 126.

Figure 3A:
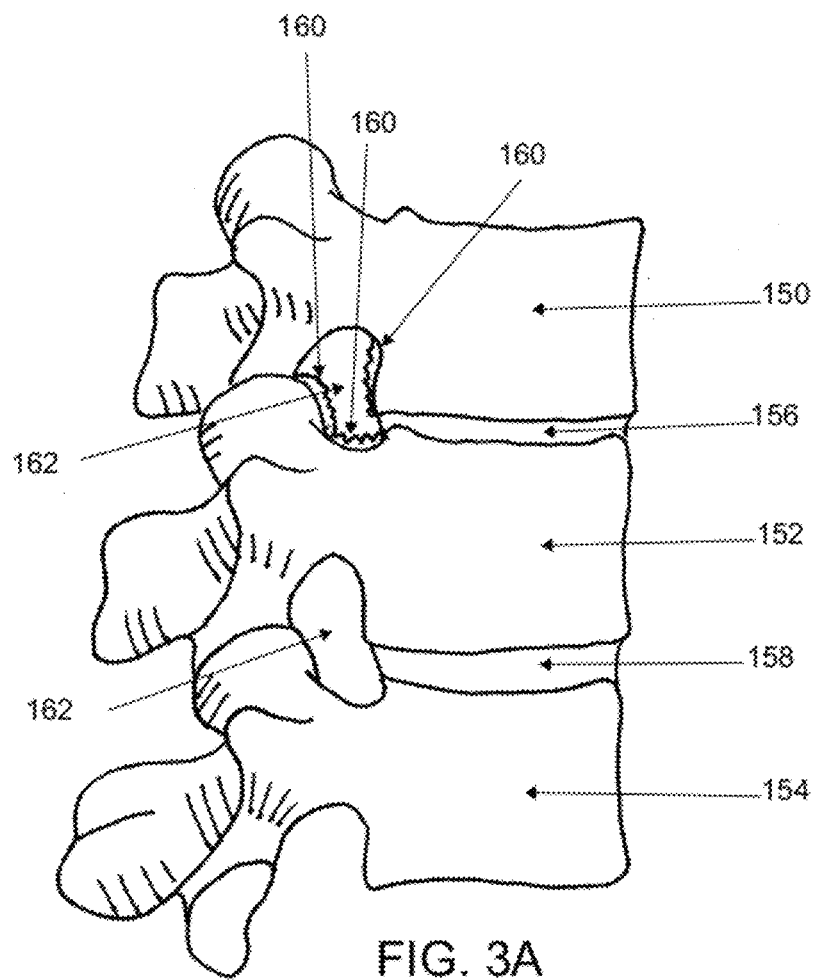
FIG. 3A is a schematic lateral view of a portion of a lumbar spine (without the spinal nerves)
Figure 3B:
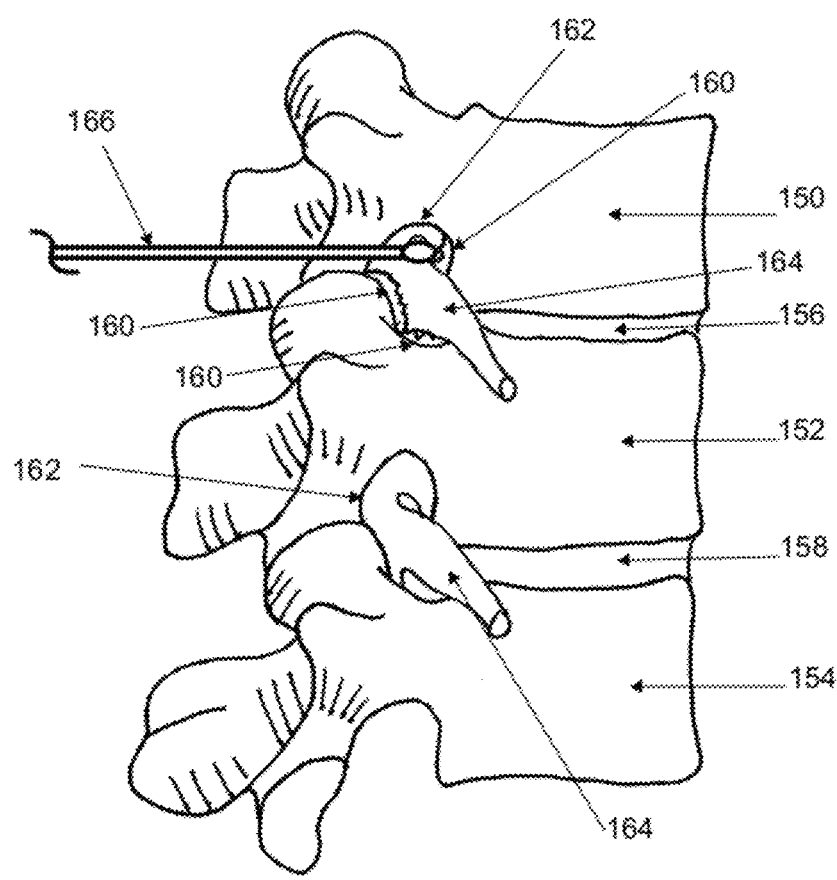
FIG. 3B depicts the portion of the lumbar spine in FIG. 3A (with the spinal nerves depicted)

With degenerative changes of the spine, which include but are not limited to disc bulging and hypertrophy of the spinal ligaments and vertebrae, the vertebral canal 102 may narrow and cause impingement of the spinal cord or the cauda equina, a bundle nerves originating at the distal portion of the spinal cord. Disc bulging or bone spurs may also affect the spinal nerves 124 as they exit the intervertebral foramina 126. FIG. 3A, for example, schematically depicts a lateral view of three vertebrae 150, 152 and 154 with intervertebral discs 156 and 158, without the spinal cord or spinal nerves. With degenerative changes, regions of bone hypertrophy 160 may develop about the intervertebral foramina 162. While secondary inflammation of the associated nerve and/or soft tissue may benefit from conservative therapy, the underlying bone hypertrophy remains untreated. The regions of bone hypertrophy 160 may be removed, with or without other tissue, using open surgical spine procedures, limited access spine procedure, percutaneous or minimally invasive spine procedures, or combinations thereof. FIG. 3B depicts the vertebrae 150, 152 and 154 of FIG. 3A with their corresponding spinal nerves 164 during a foraminotomy procedure using a burr device 166, but any of a variety of bony or calcified tissue removal devices may be used, including those described in U.S. Provisional Application Ser. No. 61/384,463, which was already incorporated by reference in its entirety, as well as the cannulotome devices described herein. One example of a limited access spine procedure is disclosed in U.S. Pat. No. 7,108,705, which is hereby incorporated by reference in its entirety. Examples of percutaneous or minimally invasive spine procedures may be found in U.S. Pat. No. 4,573,448, U.S. Pat. No. 6,217,5009, and U.S. Pat. No. 7,273,468, which are hereby incorporated by reference in their entirety.

In one particular embodiment, a patient is placed into a prone position with a pillow or other structure below the abdomen to limit lumbar lordosis. The patient is prepped and draped in the usual sterile fashion and anesthesia is achieved using general, regional or local anesthesia. Under fluoroscopic guidance, a sharp tipped guidewire, or a needle with a guidewire is inserted into the paravertebral space or epidural space from a posterior or postero-lateral location of the patient's back. In alternate embodiments, an anterior procedure through the abdominal cavity or anterior neck region may be performed. Once access to the target location is confirmed, an introducer or cannula may be inserted over the guidewire, followed by subsequent guidewire removal and insertion of an endoscope into the introducer or cannula. Alternatively, an endoscope may be inserted over the guidewire. The endoscope may be manipulated or steered to directly visualize and identify the relevant structures such as the disc, the nerve or other adjacent structures and site(s) of bone removal. In some embodiments where the patient is under local or regional anesthesia, the suspected nerve impingement may be confirmed by contacting or manipulating the suspected nerve with the endoscope, or other instrument inserted through the endoscope, and assessing the patient's response or symptoms.

Once the target region has been evaluated, any of a variety of treatments may be performed, including but not limited to the application of anti-inflammatory and analgesic agents, and the lysis of adhesions. Other treatments may include the use of a tissue removal device to remove bony tissue or hardened or calcified soft tissue to alleviate the suspected nerve or cord impingement. The tissue removal device may comprise an energy transmission device, such as a laser device manufactured by Trimedyne Inc. (Irvine, Calif.) or an ablation device produced by Arthocare Corporation (Austin, Tex.). The tissue removal device may also comprise a mechanical device such as a rotating burr, a rongeur, a reamer, a rasp, or a curette. Examples of various tissue removal devices are disclosed in greater detail below.

Figure 4A:
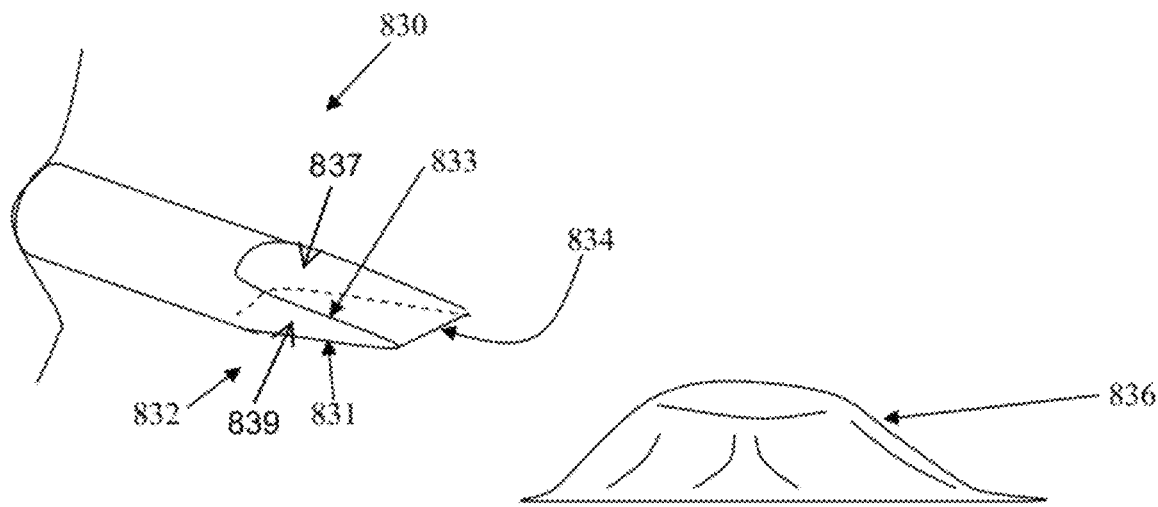
FIGS. 4A and 4B schematically depict the removal of an osteophyte using a percutaneously inserted cannulotome device.
Figure 4B:
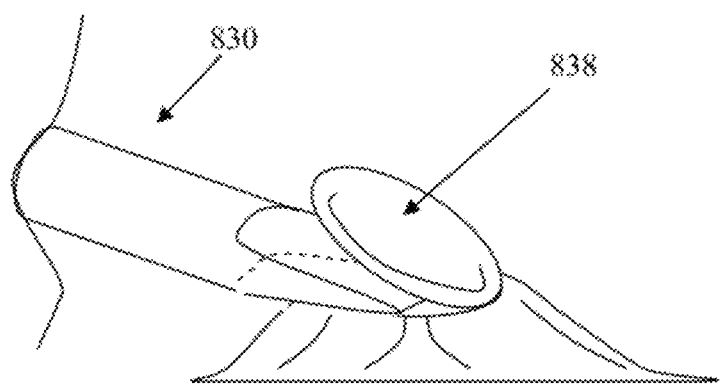
Figure 4C:
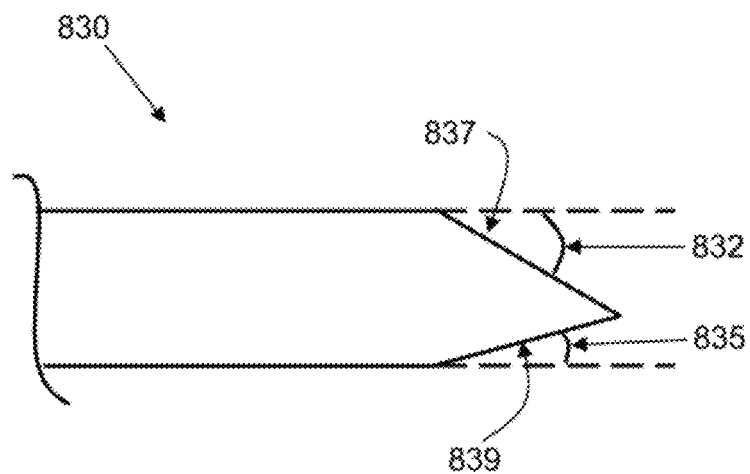
FIG. 4C is a side view of the distal end of a cannulotome device.

FIGS. 4A and 4B depict one variation of a trephine 830 that may be used to remove tissue. The distal portion 832 of the trephine 830 may have a tapered or angled shape, with a flattened tip 834. The distal portion 832 may be tapered such that the angle formed by the intersection of the bottom edge 831 and the top edge 833 of the distal portion 832 may be from about 5° to about 75°, e.g., about 10°, 20°, 30°, 45°, or 60°. FIG. 4C is a side view of the tapered distal portion 832. The top face 837 of the distal portion 832 may be form an angle 832 with respect to the line extending from the top of the shaft of the trephine 830, where the angle 832 may be from about 0° to about 90°, e.g., about 10°, 30°, 50°, 75°, or 90°. The bottom face 839 may form an angle 835 with the line extending from the bottom of the shaft of the trephine 830, where the angle 835 may be from about 0° to about 90°, e.g., about 10°, 30°, 50°, 75°, or 90°. The angles 832, 835 may be the same, such that the taper of the distal portion 832 is symmetric. In other variations, the angles 832, 835 may be different, such that the taper of the distal portion 832 is asymmetric. For example, the angle 832 may be 0°, while the angle 835 may be about 15° or more. The tip 834 of the trephine 830 may have a relatively sharp edge that may be used to remove a portion of a bone stenosis or spur 836. For example, the trephine 830 may be made of a titanium alloy, a hard steel or stainless steel material. The tip 834 may have a variety of shapes as suitable for debulking tissue, for example, the tip 834 may be pointed, angled, beveled, notched etc. The trephine 830 may be used in a scraping and/or chiseling motion to shave away portions of the bone spur 836. Additionally or alternatively, the trephine 830 may be used to remove tissue or bone by chiseling in a variety of motions, such as lateral motion, rotational and/or axial motion, etc. For example, moving the relatively sharp tip 834 of the trephine 830 towards and away from the bone spur 836 to contact the spur in an abrupt motion may cleave a portion of the bone spur, e.g., bone shaving 838. Such shaving or chiseling motion may be supplied manually by tapping the trephine externally with a hammer or mallet, or may be supplied by a reciprocating motor, for example. A distal portion of a trephine may also be textured to at least partially engage the tissue and to prevent slippage of the trephine as it scrapes against the tissue. For example, the distal tip may have burrs, ridges, grooves, hooks, or any textured pattern that may provide at least some frictional engagement between the trephine and the tissue.

Figure 5A:
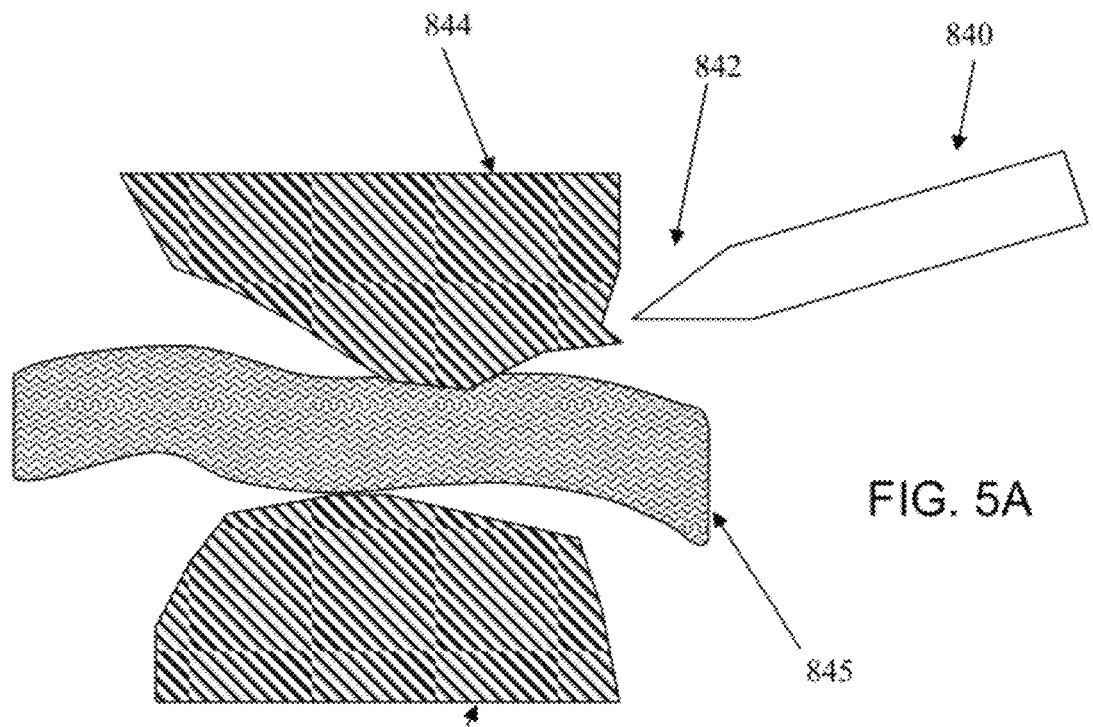
FIGS. 5A and 5B schematically depict the removal of an osteophyte located at a vertebral foramen using the cannulotome in FIGS. 4A and 4B.
Figure 5B:
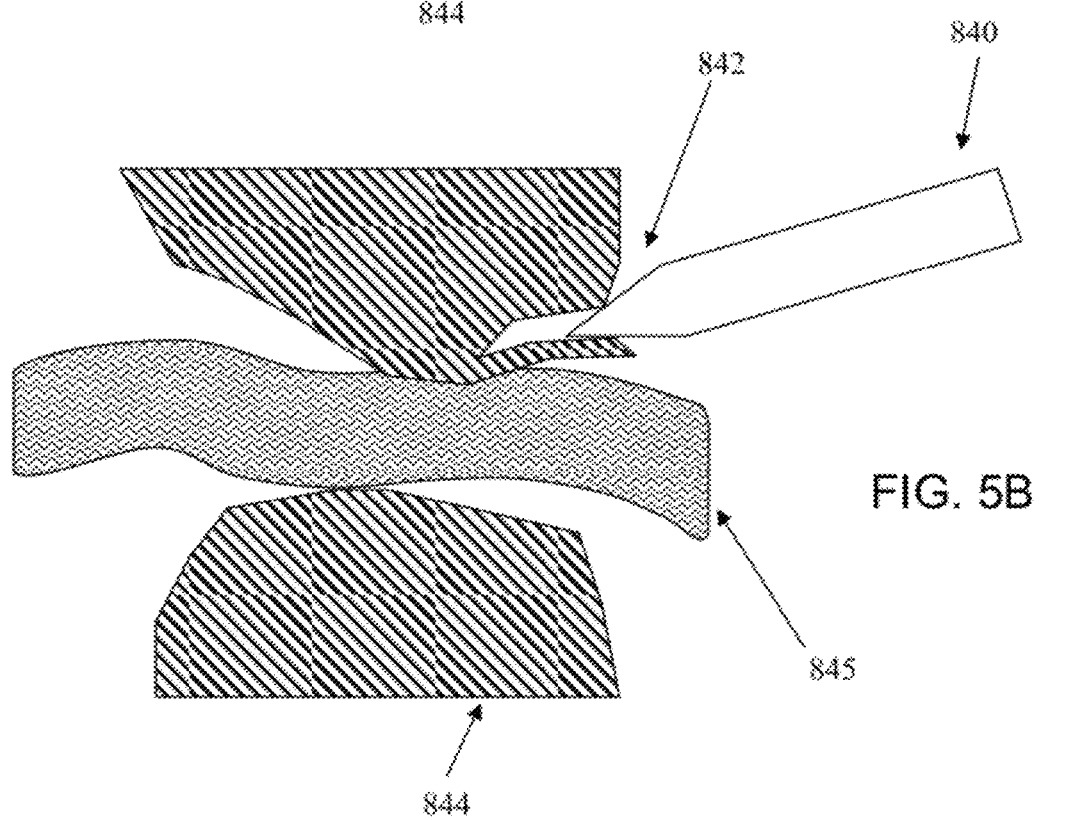

The geometry of the distal portion of a trephine may be selected to facilitate the removal of bone without impacting nerves that are in close proximity with the bone. FIGS. 5A and 5B depict the use of a trephine 840 with a tapered distal portion 842 that may be suitable for removing portions of bones 844 that impinge on a nerve 845. The tapered geometry of the distal portion 842 may help the practitioner shave away portions of the bone 844 that are close to the nerve 845 without damaging the nerve. In some variations, the distal portion 842 may be configured to be sharp enough to shave and/or scrape away the bone 844, but not sharp enough to damage the nerve 845.

Figure 4D:
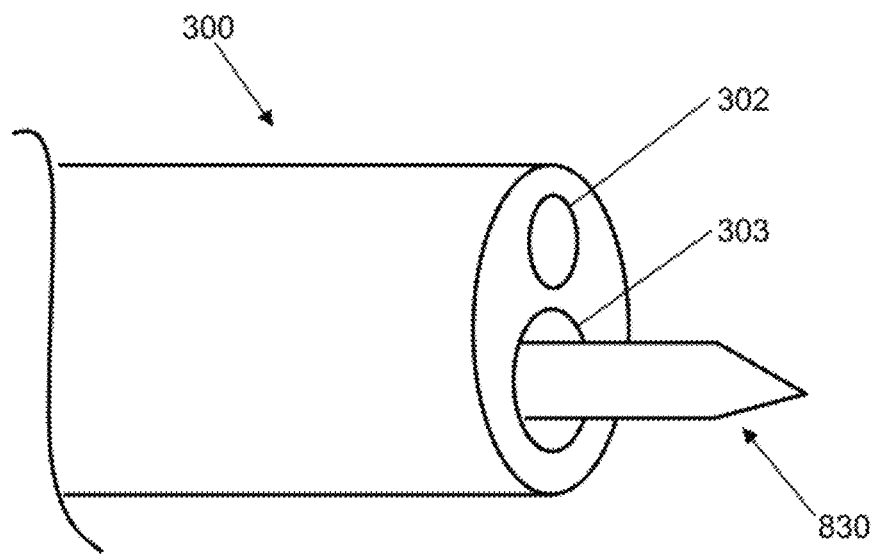
FIG. 4D is a schematic depiction of an endoscope with a cannulotome device inserted therethrough.

In some variations, a trephine may be used to contact tissue through a working lumen of an endoscope. For example, as schematically depicted in FIG. 4D, the trephine 830 may be inserted through a working lumen 303 of a rigid endoscope 300. The working lumen 303 may be located adjacent to other lumens or channels of the endoscope 300, for example, imaging channel 302. This may allow a practitioner to visually confirm the target tissue before it is removed, as well as to visually inspect and/or monitor the progress of tissue removal. Further examples are described in U.S. patent application Ser. No. 12/582,638 filed on Oct. 20, 2009, which is hereby incorporated by reference in its entirety.

The trephines described and depicted in FIGS. 4A and 4B, and 5A and 5B may be solid structures, but in other variations, such trephines may have a longitudinal lumen or channel therethrough. The lumen or channel may be used to draw tissue away from the tissue removal site, e.g., by suction. Optionally, an Archimedes screw may also be provided in the lumen to mechanically draw tissue through the lumen. The lumen may also be used for fluid infusion, for example, to flush debris away from the tissue removal site. The lumen may also be used for the delivery of pharmacological agents, contrast agents, and/or lubricants, as may be desirable.

Figure 6A:
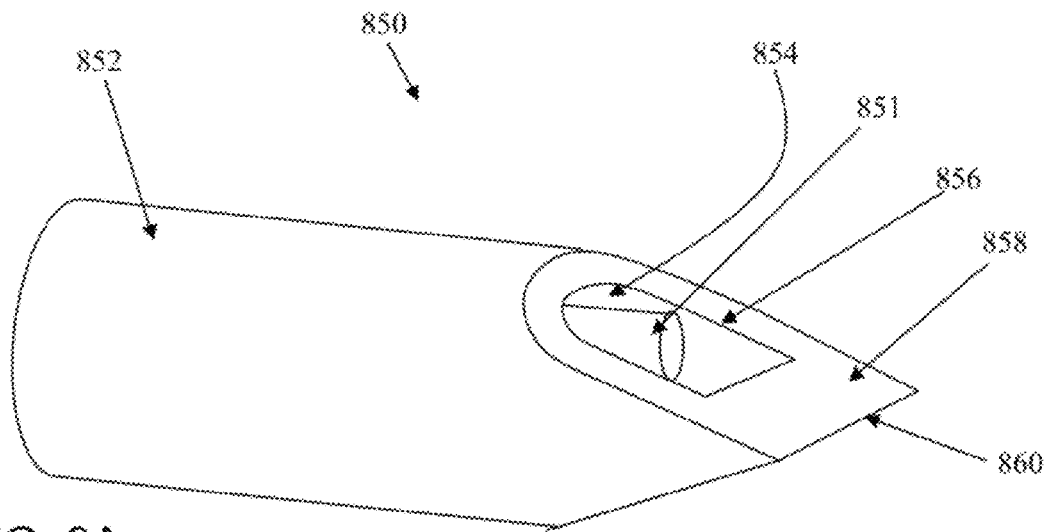
FIG. 6A is a perspective view of another example of a cannulotome device with an endoscope lumen.
Figure 6B:
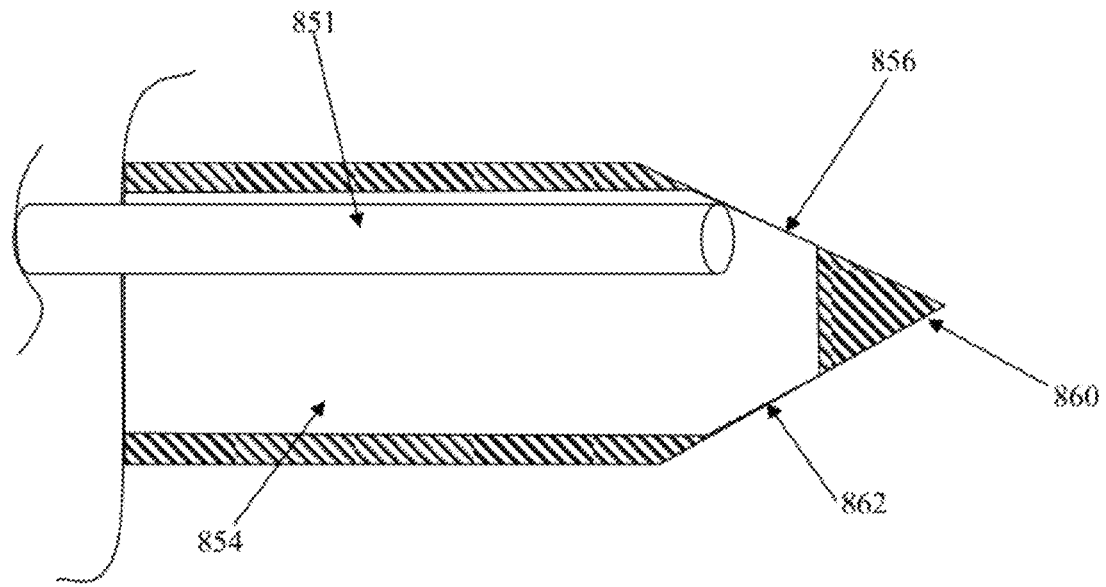
FIG. 6B is a longitudinal cross-sectional view of the cannulotome.

Additionally or alternatively, a longitudinal lumen may be used for the insertion of a fiberscope or an endoscope therethrough. For example, FIG. 6A depicts a tissue removal device or cannulotome 850 may have an elongate shaft 852 with a longitudinal lumen 854 extending through a portion of the shaft. The lumen 854 may terminate at a first opening 856 at the distal portion of the cannulotome 850, for example, on a first angled surface 858 at a distal cutting tip 860. In some variations, the lumen 854 may have a second opening 862, which may be seen in the cross-sectional view of the cannulotome 850 depicted in FIG. 6B. An endoscope 851 may be slidably inserted into the cannulotome 850, and may be able to capture images from either the first opening 856 or the second opening 862, as desired. The endoscope 851 may be guided to either the first opening 856 or the second opening 862 by bending, rotating, etc. The range of motion of the endoscope within the cannulotome lumen may be determined in part by the size and shape of the endoscope with respect to the lumen (e.g., where the lumen diameter is substantially larger than the endoscope diameter, the endoscope may be able to bend and rotate, where the lumen diameter is comparable or only slightly larger than the endoscope diameter, the endoscope may be constrained from bending). The shaft 852 of the cannulotome may have a length of about 2 in to about 8 in, and may have a diameter of about 0.5 mm to about 15 mm. In some variations, an endoscope may have a rigid shaft (such as a Wolf scope), while in other variations, the endoscope may have a flexible viewing cable (such as a fiberscope). Examples of endoscopes that may be used in conjunction with the exemplary embodiments described herein include rigid endoscopes manufactured by Richard Wolf (Vernon Hills, Ill.), Joimax (Irvine, Calif.), or Karl Storz (Tuttlingen, Germany), or flexible endoscopes manufactured by Vision Sciences, Inc. (Orangeburg, N.Y.) or Olympus (Center Valley, Pa.).

Figure 7:
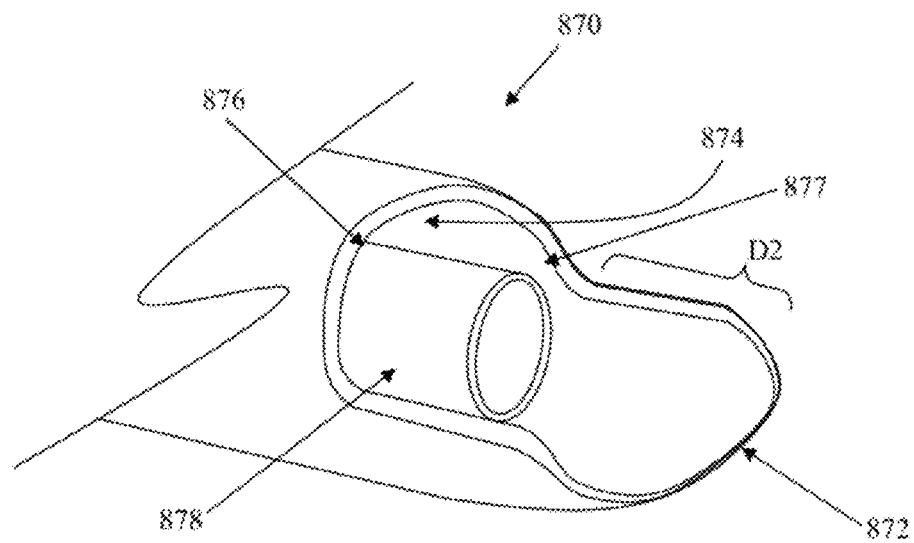
FIG. 7 is a perspective view of another exemplary cannulotome with a protruding asymmetric cutting edge.

In some variations, a lumen of a cannulotome may terminate a single opening at the distal portion of the cannulotome. In FIG. 7, for example, a cannulotome 870 may have a lumen 874 that terminates at an opening 876. The opening 876 may have a sharpened distal edge 872 that protrudes from an initial plane 877 of the opening. The distal edge 872 may protrude a distance D2 from the initial plane 877, where D2 may be in the range of about 2 mm to about 8 mm, sometimes about 3 mm to about 6 mm, and other times about 4 mm or about 5 mm. The distal edge 872 may have a curved shape, similar to a portion of a circle, e.g., a semi-circle. The protrusion of the distal edge 872 may allow a wider field of a view for an endoscope 878 that is advanced through the lumen 874 to the opening 876. This may help the practitioner view the tissue region so that the desired tissue may be removed without damaging peripheral tissues.

Figure 8:
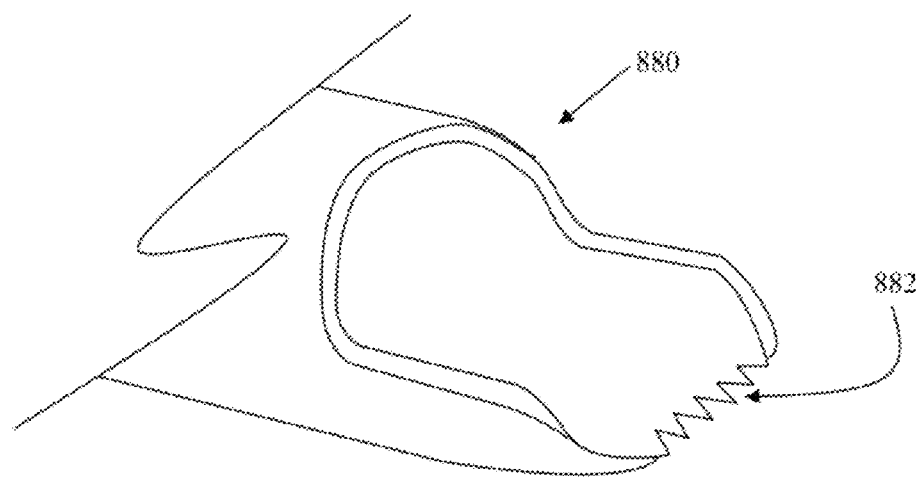
FIG. 8 is a perspective view of another exemplary cannulotome with a serrated cutting edge.
Figure 9A:
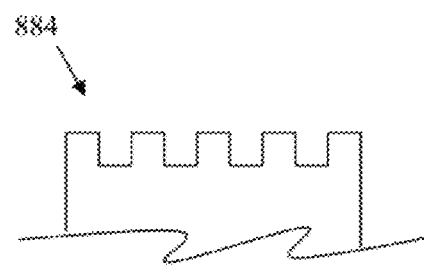
FIGS. 9A and 9B are schematic superior views of other cutting edge configurations that may be used with a cannulotome.
Figure 9B:
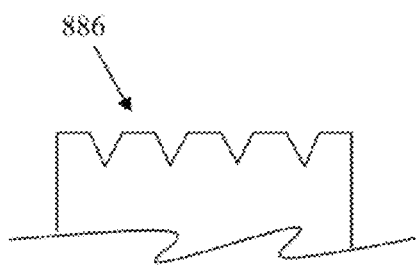

In another variation of a cannulotome 880 depicted in FIG. 8, the distal edge 882 may be curved and be serrated with teeth of various shapes and sizes. In some variations, the distal edge may have square teeth 884, as illustrated in FIG. 9A, while in other variations, the distal edge may have saw teeth 886, as illustrated in FIG. 9B. The size and shape of the teeth, angle of serration between the teeth and other parameters may be selected to be appropriate for the mechanical characteristics of the tissue to be removed. For example, the teeth 884 and 886 depicted in FIGS. 9A and 9B are generally symmetrical, but in other variations, the teeth may be asymmetrical, e.g. shaped like right-triangles.

Figure 10:
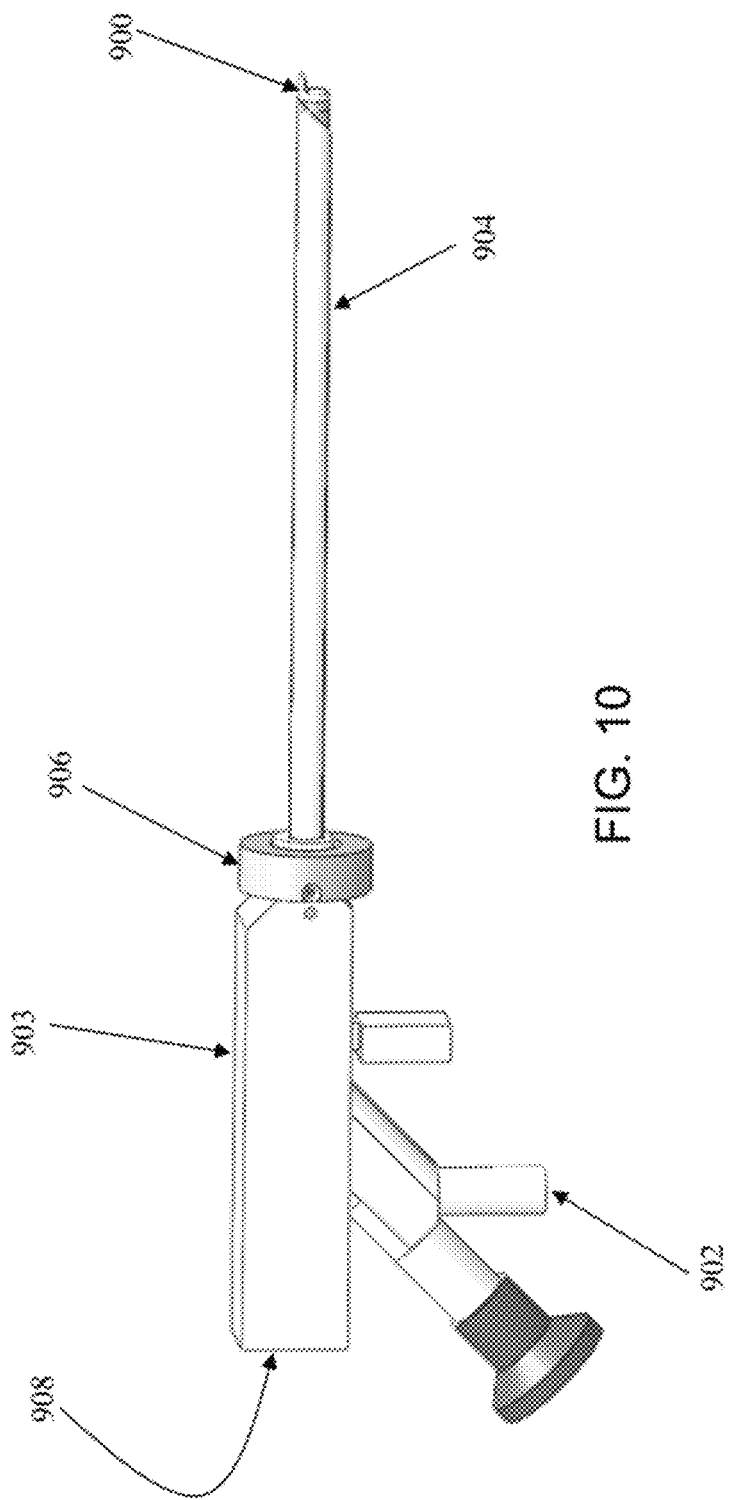
FIG. 10 is a side elevational view of another exemplary cannulotome device attached to an endoscope.

As noted earlier, the cannulotomes described herein may be used with one or more cannula systems to help provide access to the targeted tissue site. For example, the cannulotomes described herein may be used with a retractor cannula, which may comprise a rigid shaft and jaws at the distal end of the shaft. In use, the retractor cannula may be advanced to the tissue site, and the jaws may be used to manipulate and/or contact tissue. The tissue may be confirmed by visual inspection using an endoscope inserted through the retractor cannula. A cannulotome may then be advanced through the retractor cannula to contact and remove tissue. The jaws of the retractor cannula may be used to re-position the tissue during the procedure, and/or to grasp tissue for removal. In other variations, a grasping device may be advanced through a lumen of a cannulotome, such that tissue removed by the cannulotome may be grasped and drawn away by the retractor cannula jaws. Additional examples of cannula systems that may be used with any suitable cannulotomes are further described in U.S. patent application Ser. No. 12/582,638 filed on Oct. 20, 2009, which was previously incorporated herein by reference in its entirety. Another example of a cannula and endoscope system that may be used with a cannulotome 900 is depicted in FIG. 10. An endoscope 902 may be inserted through the cannulotome 900 to help provide visualization during the use of the cannulotome. A proximal handle hub 906 of the cannulotome 900 and a cannulotome handle 903 may releasably interface with the endoscope 902, such that the endoscope and the cannulotome may move in concert or may be detached as desired. For example, as shown in FIGS. 11A and 11B, the cannulotome handle 903 may have a groove 905 that may be sized and shaped to releasably and/or fixedly engage an endoscope. The cannulotome 900 may be slidably inserted through a cannula 904 to access the targeted tissue site. In use, the cannula may be stationed at the targeted tissue region, while the cannulotome 900 is moved within the cannula 904 as previously described to remove a portion of tissue. In some examples, the endoscope 902 and cannulotome 900 may be attached together, and a mallet may be used to strike the proximal ledge 908 of the cannulotome handle 903 to cause the sharpened distal tip of the cannulotome to remove tissue. The distal end of the cannula 904 may be beveled to help provide improved access to certain anatomical structures. Non-limiting examples of endoscopes 902 that may be used with the cannulotome 900, or to which the cannulotome may be adapted for use with, may include the endoscopes devices manufactured by Olympus, Pentax, Fujinon, ACMI, Machida, and the like. For example, an endoscope that may be used with the cannulotomes and endoscope retaining devices described herein may have a length of about 40 cm to about 400 cm, with a typical length of about 300 cm, and a diameter of about 1 mm to about 4 mm, with a typical diameter of about 2 mm.

Figure 12A:
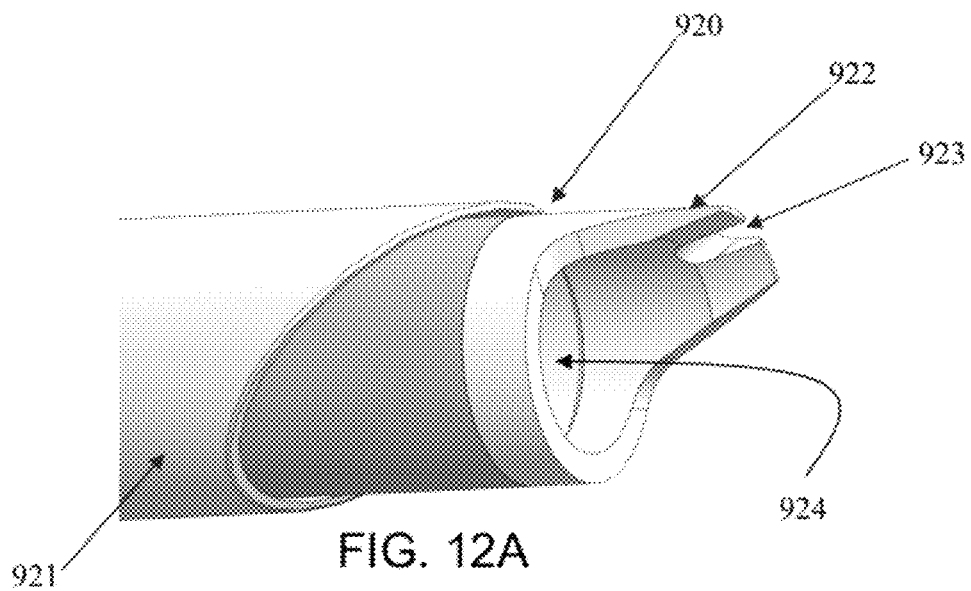
FIGS. 12A and 12B are various perspective views of the distal region of the cannulotome device depicted in FIG. 10 and FIGS. 11A and 11B.
Figure 12B:
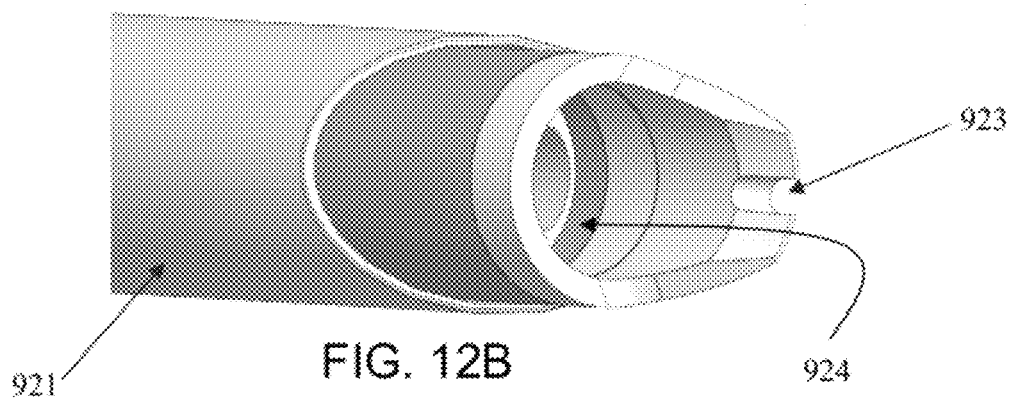
Figure 12C:
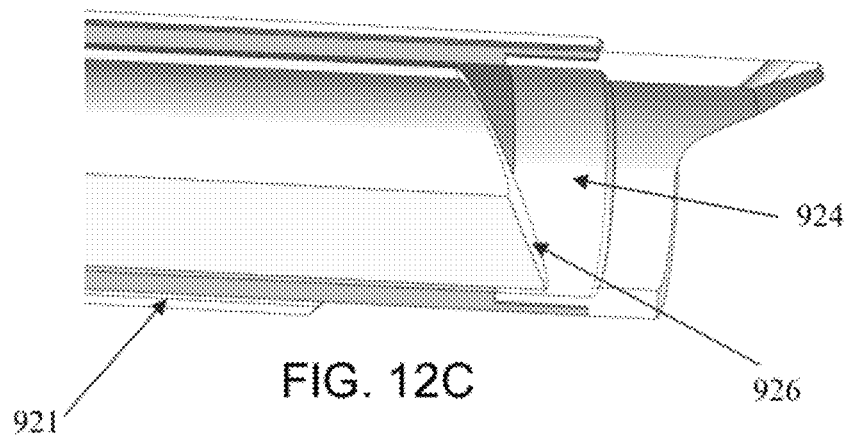
FIG. 12C is a longitudinal cross-sectional view of the distal region of the cannulotome device depicted in FIGS. 12A and 12B.
Figure 12D:
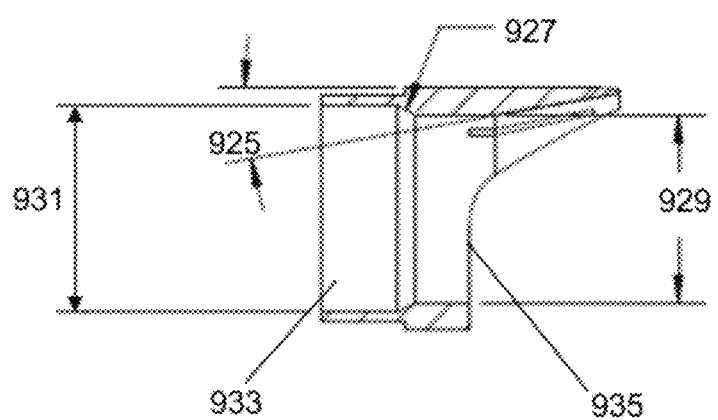
FIG. 12D is a schematic cross-sectional view of the distal cutter of the cannulotome device depicted in FIGS. 12A and 12B.
Figure 12E:
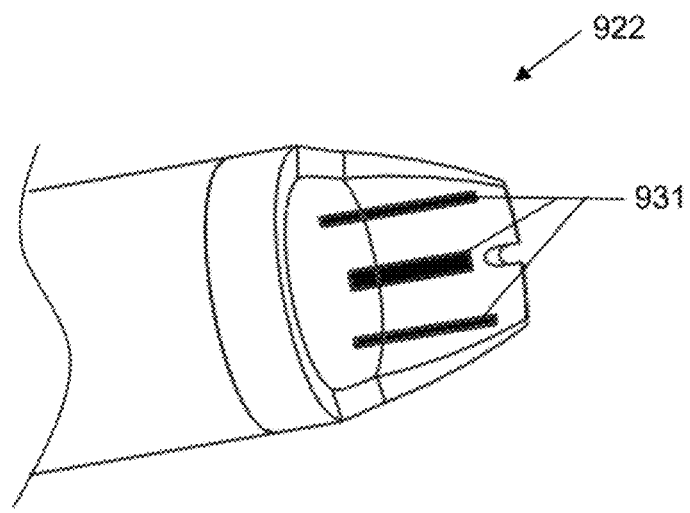
FIG. 12E is an inferior perspective view of the distal cutter of the cannulotome device depicted in FIGS. 12A and 12B.

The position of an endoscope and/or endoscope retaining device within a cannulotome may be adjusted as needed in the course of the procedure. For example, the endoscope may be retracted from the distal end of the cannulotome during some parts of the procedure and extended through the cannulotome for other parts of the procedure. Accordingly, the distal end of a cannulotome may be capable of accommodating a relatively thicker wall section. Similarly, a cannulotome may be retracted from and/or extended through an introducer cannula. The distal end of the cannulotome may exit the distal opening of the introducer cannula to contact and remove tissue. FIGS. 12A to 12C depict a cannulotome 920 inserted through a cannula 921, where the cannulotome 920 has a wedge-shaped or tapered distal cutter portion 922. The cannulotome may comprise an elongate shaft with a lumen terminating at a distal opening. The distal opening may comprise a perimeter, where the distal cutter 922 is may be eccentrically or non-uniformly located around the perimeter of the distal opening. In some variations, the eccentric configuration of the distal cutter 922 with respect to the longitudinal central axis of the elongate shaft may help facilitate the removal of bone along the periphery of the cannulotome (e.g., for cutting out an arc that approximates the radius of curvature of a cannula device, e.g., cannula 921, to advance the cannula device to target tissue). This cutting may be performed by rotating the eccentric cutter around its longitudinal central axis during the hammering. In contrast to a trephine device, which typically has a cutting structure comprising a plurality of teeth that are uniformly distributed around a circular perimeter, and turned multiple times to cut out a pathway (see, for example, FIGS. 20A and 20B in U.S. Provisional Application 61/384,463), cannulotome 920 is configured to utilize a chisel-like action that concentrates the cutting force on only a small arc of the target tissue at any given time, which may provide greater cutting efficiency and generate less heat. Using a cutter edge that is configured to cut in small arcs may also help target removal of discrete portions of soft tissue or bone, and help avoid cutting or damaging targeted and non-targeted soft tissue or bone. The distal cutter 922 may comprise a tapered protrusion, where the tapered protrusion comprises a proximal base and a distal cutting edge, and wherein at least one-quarter of the perimeter lies at or proximal to the base. While a first portion of the perimeter of the distal opening may have a cutting edge, a second portion of the perimeter may have a non-cutting surface. The cutter 922 may be thicker proximally, and may taper down to a thin arc at the distal-most end. In some variations, the cutter 922 may be integrally formed with the elongate shaft, while in other variations, the cutter may be separately formed from the shaft and attached (e.g., by welding, soldering, friction-fit, screw-fit, etc.). The distal-most end may have a cutting surface that is semi-sharp (e.g., may have an acute or sharp angle, and/or may be rounded with a radius of about 0.0005 in to about 0.002 in) to allow for bone cutting with axial tapping on the proximal end. Alternatively, the distal-most end may be relatively blunt (e.g., may have a radius of about 0.002 in to about 0.01 in, or 0.01 in to 0.02 in). A relatively blunt distal-most end may be used to fracture bone while reducing unwanted cutting of nerves and/or surround soft tissue. In some variations, the distal-most end may not be rounded, but may have a flattened cutting surface. The wedge-shape of the distal cutter 922 may help to prevent the cutting edge from getting stuck in bone as it cuts into the bone/ligament. The wedge angle may be from about 15° to about 45° degrees, e.g., about 10°, or 20°, or 30°. Additionally, the wedge shape may help to separate the bone/ligament from its matrix as the distal cutter 922 is progressively driven into the target tissue medium. This may allow for a rongeur or a grasper to be inserted through a working lumen 924 to grasp the separated tissue for removal (the working lumen 924 may also be used to insert an endoscope 926). In the longitudinal section, the distal cutter 922 may be wedge-shaped, but in the transverse section, the distal cutter may have an arc shape occupying a sector of about 20° to about 90°, e.g., about 60°, of the cannulotome. The distal cutter 922 may have a wedge or bevel angle 925 of about 5° to about 90°, e.g., about 10° or about 20°, as illustrated in FIG. 12D. The distal cutter 922 may have a proximal lumen 933 with a diameter 931 from about 0.240 in to about 0.244 in, e.g., about 0.242 in. A distal opening 935 may have a diameter 929 from about 0.218 in to about 0.222 in, e.g., about 0.220 in. A chamfer 927 may have a length of about 0.11 in, and may form a 60° with respect to the surface of the distal opening 935. The cutting edge may be serrated, or may have one or more slots or notches 923. The slots or notches may help to concentrate the cutting forces onto a smaller surface area, or may allow for sawing action when the cannulotome 920 is rotated to help further expand the cutting to larger arc, for example. The proximal-most portion of the 923 may be distal to a proximal base of the tapered protrusion, and/or may not contact or extend proximally beyond the distal opening of the cannulotome elongate shaft. The distal cutter 922 may be attached to the shaft by mechanical interlocks, soldering, welding, or gluing, or it may also be a continuation of the shaft of the cannulotome 922. The distal cutter may be made of stainless steel, titanium alloy, tungsten carbide, ceramic, or glass, e.g., it may be made of 17-4 or 400 series stainless steel. In some variations, the distal cutter may be heat treated to maximize yield strength and hardness for robustness in cutting bone and tough ligaments.

In some variations, the distal cutter 922 may comprise one or more markings 931 on the internal surface of the opening and/or lumen. Such markings may be used to facilitate positioning of the endoscope and/or endoscope retaining device. The markings may be used to indicate orientation or assist the user in aligning the endoscope by visualizing the inner surface of the distal cutter with the endoscope, and may also help to identify the location of the cutter 922 with respect to surrounding tissue. In some variations, the markings may comprise one or more lines parallel to a longitudinal axis of the cannulotome. Additionally or alternatively, the markings may comprise one or more lines perpendicular to a longitudinal axis of the cannulotome, and in some cases, may form a gridded pattern that allows a user to visualize both longitudinal and lateral movements of the cannulotome. The markings may also help to orient and position a device that may be advanced through the working lumen 924. The markings 931 may be provided on the cutter 922 using any suitable methods, including but not limited to, laser-marking, pad printing, and the like. The markings 931 may also be surface structures, such as grooves, ribs, and the like, which may be provided during the manufacture of the cutter using any suitable method (e.g., molding, laser-welding, etc.).

Figure 13A:
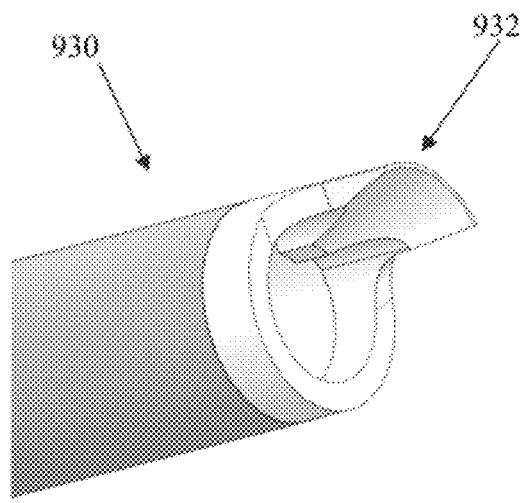
FIGS. 13A and 13B are various perspective views of the distal region of another exemplary cannulotome device.
Figure 13B:
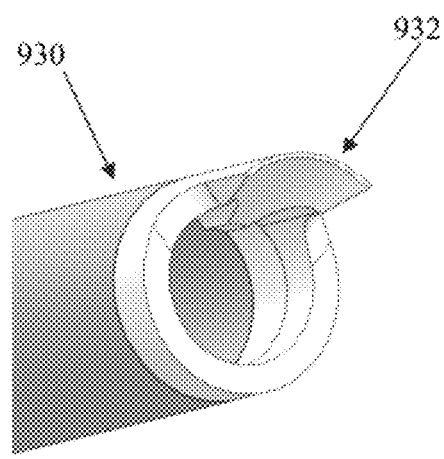
Figure 13C:
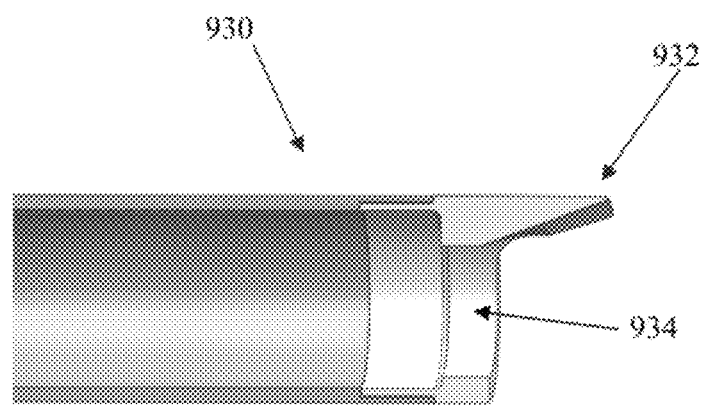
FIG. 13C is a longitudinal cross-sectional view of the distal region of the cannulotome device depicted in FIGS. 13A and 13B.

Another variation of a cannulotome 930 is depicted in FIG. 13A. The cannulotome 930 may have a distal tip 932 that is straight with a ribbed portion 934. The straight portion 936 protruding from the cannulotome 930 may be used for direct chiseling or scraping of the tissue, while the ribbed portion 934 may have an extra thickness to pry apart tissue.

Figure 16A:
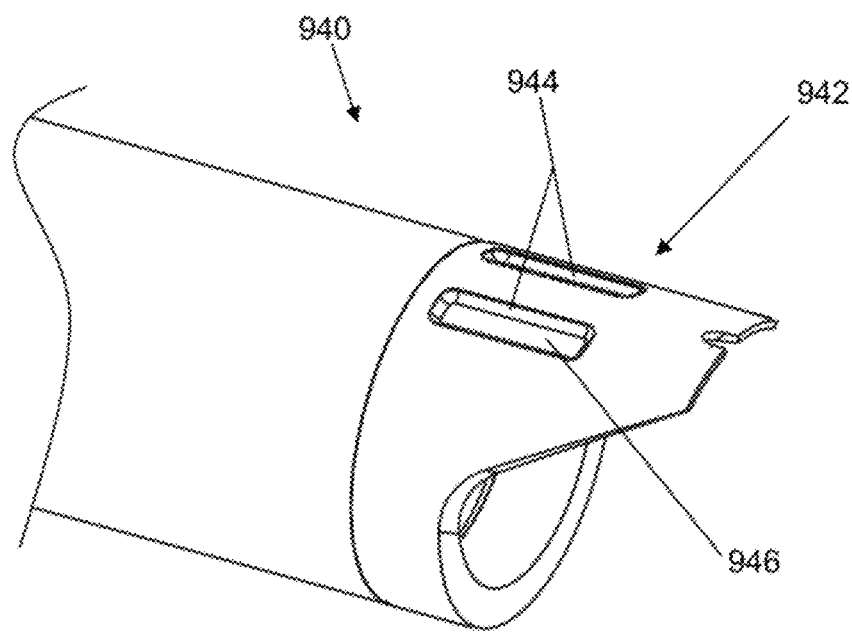
FIG. 16A is a perspective view of the distal region of another exemplary cannulotome device.
Figure 16B:
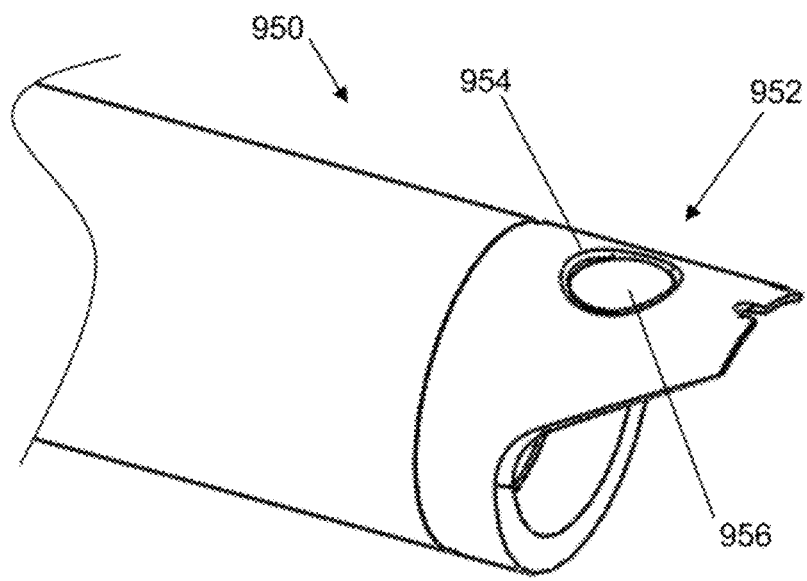
FIG. 16B is a perspective view of the distal region of yet another exemplary cannulotome device.

In some variations, the distal cutter of a cannulotome may comprise one or more recesses that may be used to help deliver therapeutic substances or mechanical agents (e.g. lubricants) to the tissue. Therapeutic substances may include anti-coagulant drugs, bone wax, and the like. Depositing the therapeutic substances in the recesses may help to ensure that the substance is applied to the target tissue and not dispersed as the cannulotome is advanced (e.g., through an introducer cannula, etc.). For example, as shown in FIG. 16A, cannulotome 940 may comprise a distal cutter 942 with two recesses 944 into which a therapeutic substance 946 has been deposited. The recesses 944 are shown to be rectangular, but it should be understood that they may have any desired shape, e.g., circular, elliptical, etc. The depth of the recesses may be uniform or non-uniform. In another example depicted in FIG. 16B, a cannulotome 950 may comprise a distal cutter 952 with a single circular recess 954 into which a therapeutic substance 956 has been deposited. While distal cutters have been illustrated as having one or two recessed regions located on a wedge portion, it should be understood that there may be any number of recessed regions (e.g., 3, 5, 6, 10, 12, etc.) located anywhere on the cutter (e.g., distributed around the distal rim of the cutter, along the distal edge of the wedge, etc.).

Figure 14:
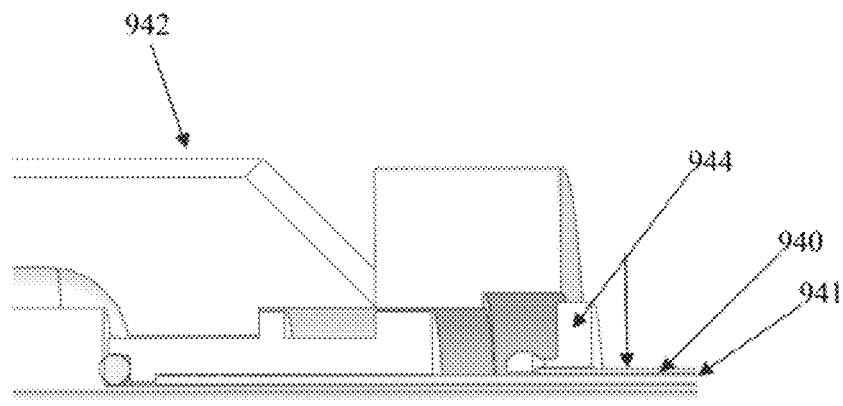
FIG. 14 is a detailed cross-sectional view through the hub region of the cannulotome in FIG. 10.
Figure 15:
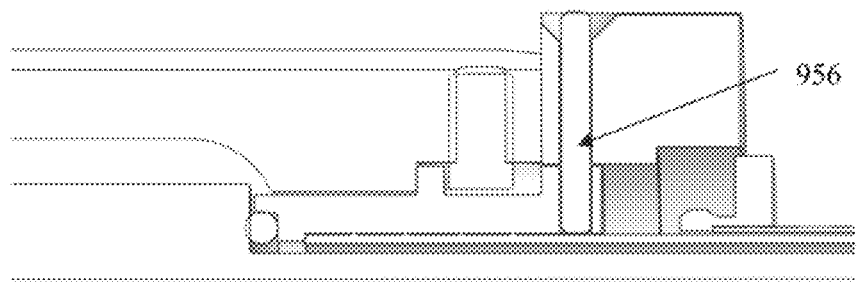
FIG. 15 is a detailed cross-sectional view of an alternate hub region configuration of a cannulotome.

A cannulotome and an endoscope and/or endoscope retaining device may be coupled or attached in any suitable manner. One example of how a cannulotome 940 may be coupled with an endoscope 946 is depicted in FIGS. 14 to 15. The cannulotome 940 is inserted through a cannula 944, and the endoscope 946 is inserted through the lumen of the cannulotome 940. A cannulotome handle knob or hub 948 may interfit with the cannula 944 and may be fixedly attached to a cannulotome spindle 950. The cannulotome spindle 950 may have one or more grooves 951 configured to interfit with any suitable screw(s). In some variations, the cannulotome spindle 950 may have one or more cannulotome o-rings 952 proximal to the grooves 951. As depicted in FIG. 15, the endoscope 946 may be attached to the cannulotome 940 at several locations. For example, one or more screws 954 may be threaded into the cannulotome handle 942, protrude into the grooves 951, and may attach the spindle 950, hub 948, and the cannulotome shaft 941 together. Pins 956 may be inserted through the hub 948 to rigidly fix the hub 948 to the spindle 950. Optionally, the spindle 950 and the cannulotome shaft 941 may be attached with a solder joint, which may help to rigidly fix the spindle to the cannulotome shaft. With these attachments, rotating the proximal portion of the cannulotome may also be rotated the distal cutting portion of the cannulotome. The cannulotome o-rings 952 may help to seat the endoscope 946 within the cannulotome handle 942. Alternatively or additionally, a cannulotome and an endoscope and/or endoscope retaining device may be coupled or attached as previously depicted and described in FIGS. 17A-17D and 21A-21B below.

Figure 17A:
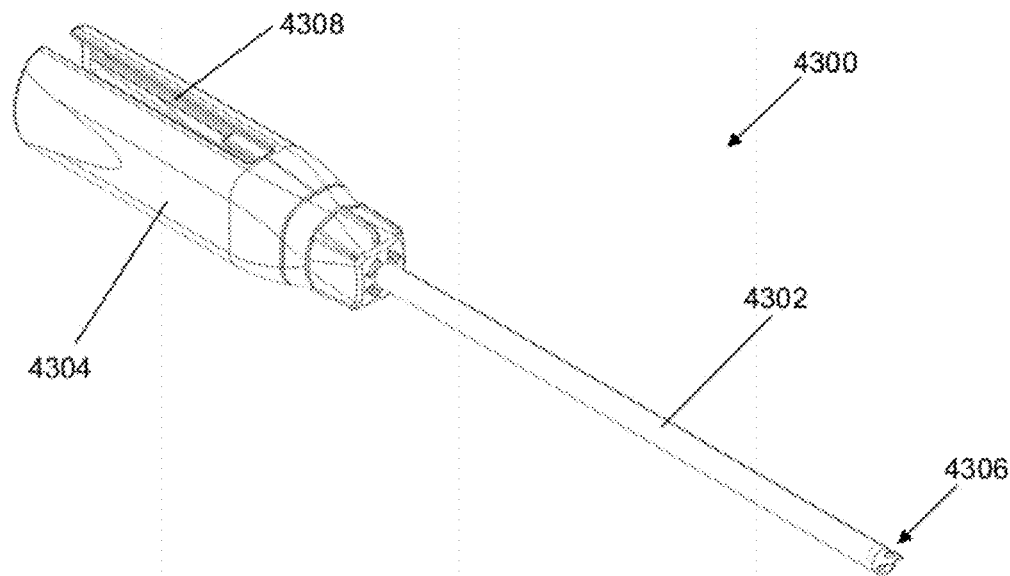
FIG. 17A is a perspective elevational view of an exemplary cannulotome.

Another variation of a cannulotome is depicted in FIG. 17A. The cannulotome 4300 may comprise an elongate shaft 4302 attached to a proximal handle 4304. The elongate shaft 4302 may comprise a cutter 4306 at its distal end. The cutter 4306 may comprise an opening that is in communication with the lumen of the shaft 4302, such that devices may be advanced from the proximal handle 4304 to the distal cutter 4306. Any of the cutters described previously may be used with the cannulotome 4300. The proximal-most surface of the handle 4304 may be a mallet-contact surface, and may be reinforced as may be desirable. The mallet-contact surface may generally be aligned along the longitudinal axis of the shaft 4302, which may allow for a direct transmission of force from the proximal handle to the distal cutter 4306. The proximal handle 4304 may also comprise a slot 4308 that is sized and shaped for slidably retaining an endoscope therein. The endoscope may be advanced through the shaft 4302 such that the distal tip of the endoscope exits the opening of the cutter. In some variations, the endoscope may be a rigid endoscope such as a Wolf scope, while in other variations, the endoscope may be a flexible endoscope or fiberscope.

Figure 17B:
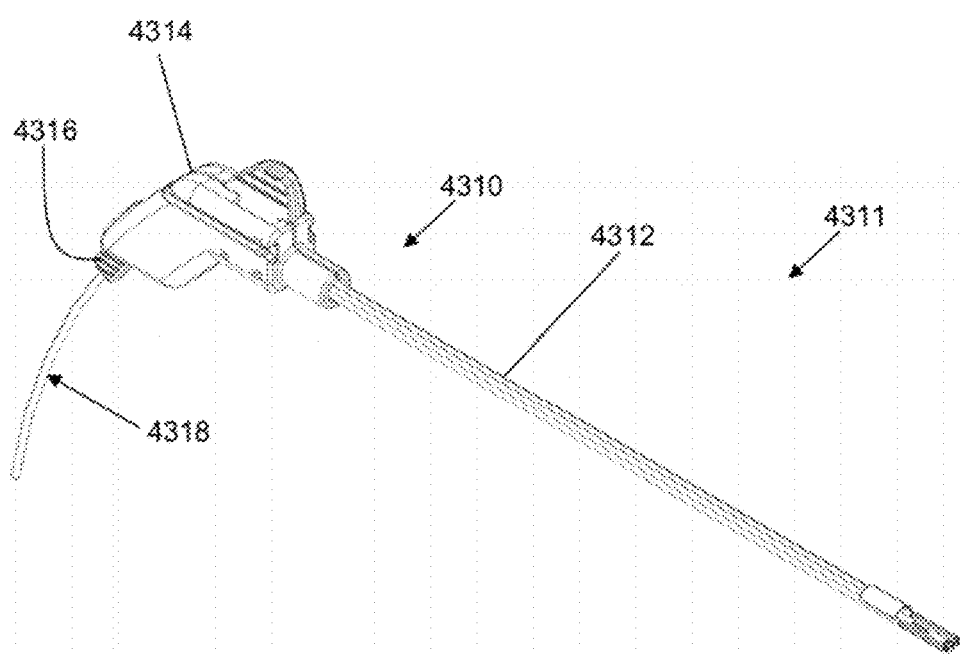
FIG. 17B is a perspective elevational view of an exemplary endoscope retaining device that may be used with the cannulotome of FIG. 17A.

An endoscope (e.g., a flexible endoscope) may be retained by a sheath and/or rail, which may help provide some rigidity, stability, and/or column strength to help facilitate the advancement of the endoscope through the shaft 4302 to the distal cutter 4306. One example of an endoscope retaining device that may be used to advance an endoscope through a cannulotome is depicted in FIG. 17B. As shown there, an endoscope assembly 4311 may comprise an endoscope retaining device 4310 and an endoscope 4318 coupled to the endoscope retaining device. The endoscope retaining device 4310 may comprise an elongate support structure or frame 4312, and a proximal handle 4314 attached to the support frame 4312. Other variations may optionally comprise an outer sheath that extends over the support frame, where the support frame may or may not be directly attached to the outer sheath. An endoscope 4318 may be coupled to the endoscope retaining device 4310 via an attachment tab 4316. For example, the attachment tab 4316 may be made of an elastomeric material, and may be temporarily or permanently attached to a portion (e.g., shaft or cable) of the endoscope 4318. The attachment tab may be made from silicone, urethane, or another suitable elastomer; the durometer range for the tab may be in the range of 40 A to 100 A. The attachment tab 4316 may be sized and shaped to mate with an opening or slot in the proximal handle 4314. For example, the width and length of the mating slot in the handle 4514 may be slightly smaller than the corresponding dimensions of the elastomeric attachment tab 4316, such that compressing the attachment tab would enable the tab to be inserted into the slot. After the external compressive force is released, the attachment tab may return to its original size and shape such that the tab along with the endoscope 4318 are secured by friction-fit within the slot. Alternatively or additionally, the proximal handle 4314 may comprise a latch that may be used to couple the flexible endoscope to the handle, as will be further described below.

An endoscope may also be coupled to the endoscope retaining device along the support frame 4312. For example, as described above, a proximal portion of the endoscope may be retained within the proximal handle, and the distal-most portion of the endoscope 4318 may be attached to the distal-most portion of the support frame 4312, as will be described below. The support frame 4312 may act as a track or a rail along which a flexible endoscope may be aligned. The support frame may be an elongate support structure with a distal securing element configured to partially enclose a distal circumferential surface of an endoscope in a predetermined rotational alignment, while partially exposing the distal circumferential surface of the endoscope. The support frame 4312 may be made of any material that is semi-rigid with some flexibility, such as sheet metal and/or plastic. This may provide some rigidity to a flexible endoscope attached thereto, which may help a practitioner to easily advance the endoscope through the shaft of a cannulotome. In some variations, there may be a coating and/or lubricant on the endoscope, and/or endoscope retaining device that may reduce the frictional forces between these devices and the cannulotome. For example, the support frame may have a coating and/or lubricant applied over its surface. An outer sheath of an endoscope retaining device may also have a coating and/or lubricant applied along its inner lumen (e.g. to reduce any frictional forces between the wall of the inner lumen and the endoscope and/or support frame) and/or along its outer surface (e.g., to reduce any frictional forces between the outer surface of the sheath and the shaft of a cannula and/or cannulotome). As will be described later, some variations of a support frame may be configured to help steer the distal portion of an endoscope to visualize the tissue region at or near the cutter 4306.

Figure 17C:
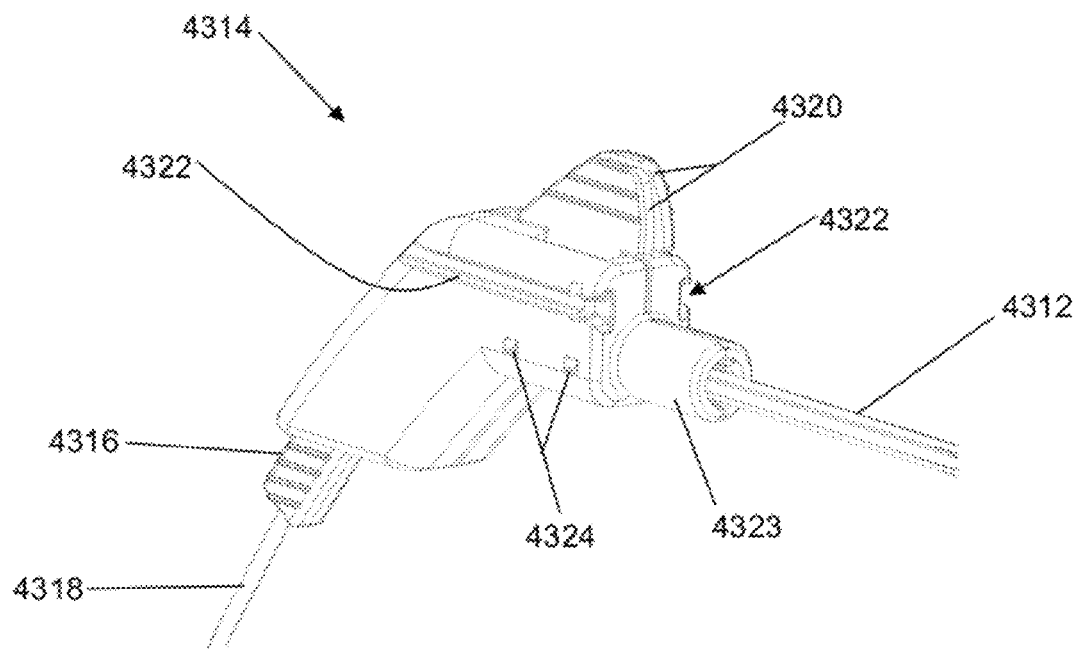
FIG. 17C is a close-up perspective view of the endoscope retaining device of FIG. 17B.
Figure 17D:
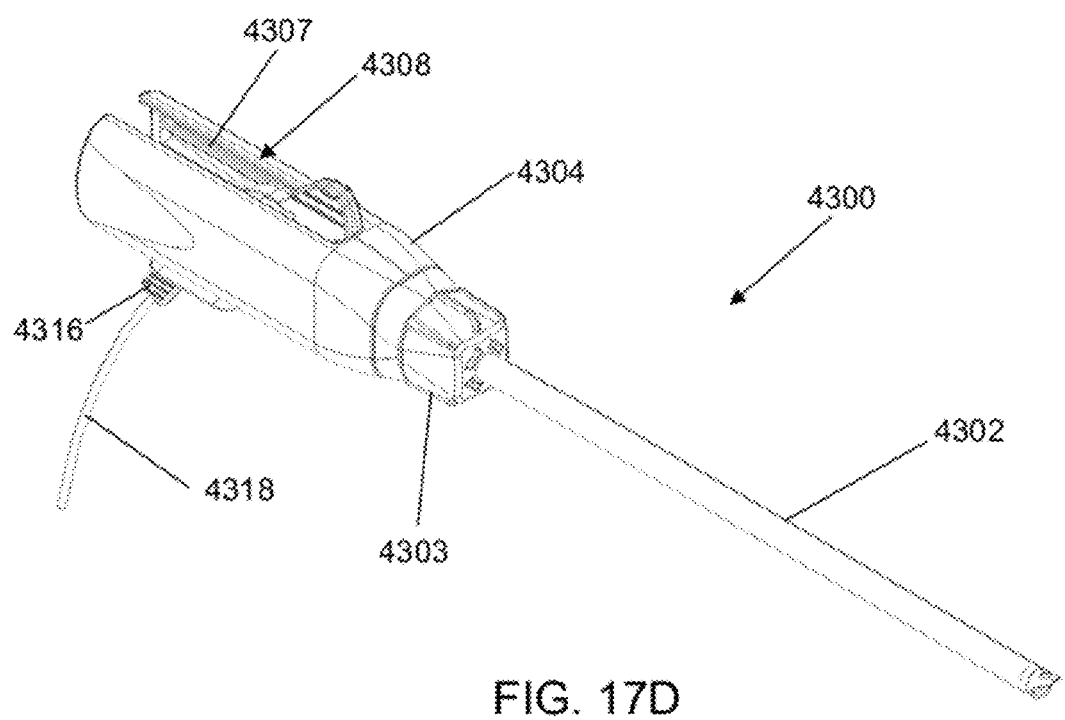
FIG. 17D depicts the endoscope retaining device of FIG. 17B coupled to the cannulotome of FIG. 17A.

FIG. 17D depicts the endoscope assembly 4311 after it has been inserted into and coupled with the cannulotome 4300. The endoscope assembly 4311 and the cannulotome 4300 may be releasably attached using any suitable mechanism. For example, as depicted in FIG. 17C, the proximal handle 4314 of the endoscope retaining device 4310 may comprise one or more flanges 4320 that may be sized and shaped to slide into and along the groove 4308 of the cannulotome handle 4300. The flanges may help position the endoscope assembly with a predetermined radial orientation with respect to the cannulotome 4300. Additionally or alternatively, the proximal handle 4314 may comprise one or more recessed tracks 4322 (e.g., one track along each side of the handle) that may correspond to one or more rails 4307 within the groove 4308 of the cannulotome handle 4304. These features may help to align the endoscope retaining device 4310 with the cannulotome 4300 such that an endoscope coupled to the support frame 4312 may be directed through the cannulotome shaft 4302. The endoscope assembly 4311 may be longitudinally slidable within the cannulotome 4300, which may allow a practitioner to adjust the field of view as imaged from the endoscope. Alternatively or optionally, the position of the endoscope assembly 4311 within the cannulotome may be locked once a desired position is attained. For example, the endoscope retaining device handle 4314 may also comprise one or more notches 4324 that correspond to one or more latches (not shown) within the cannulotome handle 4304 such that when the endoscope retaining device is fully advanced into the cannulotome handle, the latches engage the notches 4324 thereby coupling the retaining device 4310 with the cannulotome 4300. Notches may be provided anywhere along the length of the endoscope retaining device handle 4314 such that the endoscope assembly may be locked at a desired position. The handle 4314 of the endoscope retaining device may optionally comprise a collet 4323, and the handle 4304 of the cannulotome may optionally comprise a rotatable clamp 4303. When the endoscope retaining device 4310 is inserted into the cannulotome 4300, the collet 4323 may fit into the rotatable clamp 4303 such that rotating the clamp 4303 in a first direction may reduce its inner diameter and secure the collet therein. The endoscope retaining device may be released from the cannulotome by rotating the clamp 4304 in a second direction opposite to the first which may increase its inner diameter and release the collet of the endoscope retaining device. In some variations, the collet and the clamp may each comprise corresponding threads that allow the clamp to be tightened over the collet. In still other variations, a key member and/or set screw may be used to secure the collet and the clamp. The endoscope assembly and cannulotome may be coupled together using any suitable mechanism, for example, including friction-fit, snap-fit, hook-and-latch engagement, magnetic attraction, and the like. In some variations, a spring-based friction-fit between the endoscope assembly and the cannulotome may be desirable, since the friction-fit may stabilize the position of the endoscope assembly within the cannulotome, but may limit transmission of mechanical impact experienced by the cannulotome (e.g., from striking the cannulotome with a surgical mallet) to the endoscope assembly. This may mitigate potential damage to the endoscope during the procedure. In use, the endoscope assembly together with the cannulotome may be inserted through an introducer and/or retractor cannula to contact a target tissue site. In some variations, the cannulotome may be rotated and/or longitudinally translated within the introducer and/or retractor cannula.

Figure 18A:
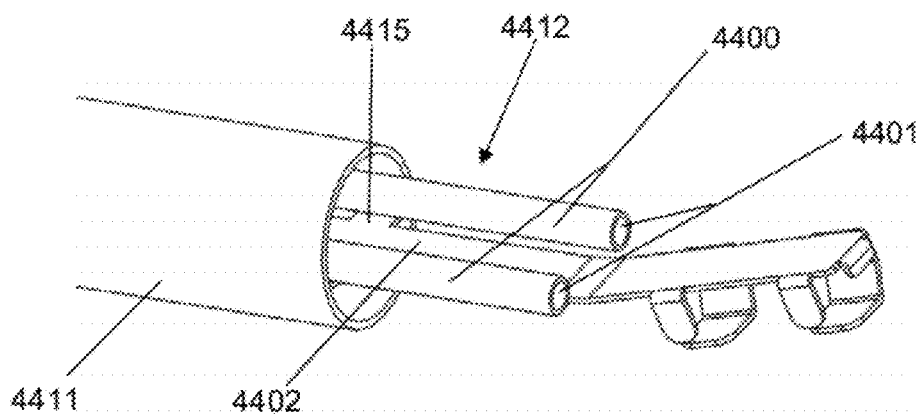
FIGS. 18A to 18C depict various perspective views of the distal end of a support frame of an exemplary endoscope retaining device.

The support frame 4312 may comprise one or more tubular structures or channels that extend from a proximal portion of the frame to the distal portion. The tubular channels may be configured to transport fluid along the support structure. Each tubular channel may comprise an external surface and an internal surface. The tubular structures may be used as fluid and/or device working lumens. For example, a flushing fluid may be infused through the tubular structures to clear debris from the distal portion of the support frame, which may aid in acquiring in clear images. Flush fluids may also help to keep debris from catching onto the front of the endoscope. FIG. 18A depicts the distal portion of a support frame 4412 extending from an outer sheath 4411 of an endoscope retaining device. The support frame 4412 may be longitudinally slidable with respect to the outer sheath 4411, and/or may be rotatable within the outer sheath 4411. In some variations, the support frame may have a fixed axial and longitudinal orientation with respect to the outer sheath. As depicted there, the support frame 4312 comprises two tubular structures 4400 arranged in parallel, each terminating at an opening 4401. The tubular structures 4400 may be coupled to an elongate strip or base 4402 of the support frame 4412. The tubular structures 4400 and the base 4402 may be made of any semi-rigid material, such as stainless steel, polyimide, nylon, PET, polyethylene, etc. The tubular structures 4400 and the base 44002 may be integrally formed or may be separately formed and attached together using any suitable method (e.g., welding, soldering, adhesive-bonding, etc.). While the variation depicted and described herein has two tubular structures 4400, it should be understood that there may be any number of tubular structures as may be desirable, e.g., 1, 3, 4, 5, 6, 8, 10, 12, 15, etc.

Figure 18B:
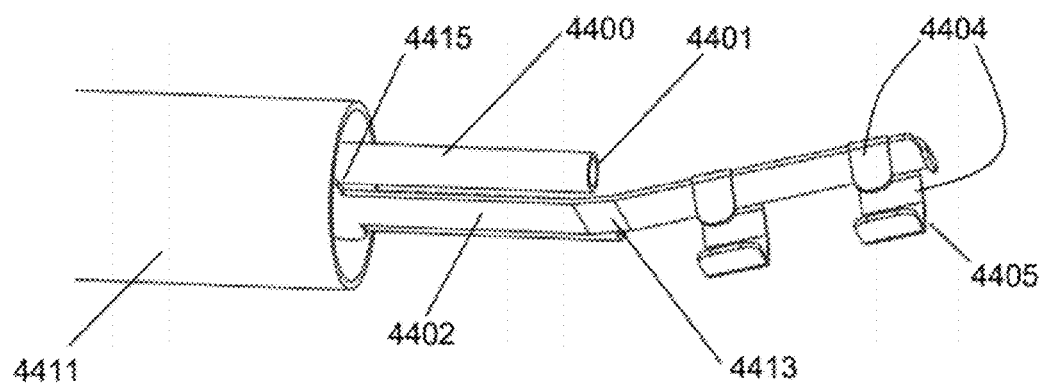
Figure 18C:
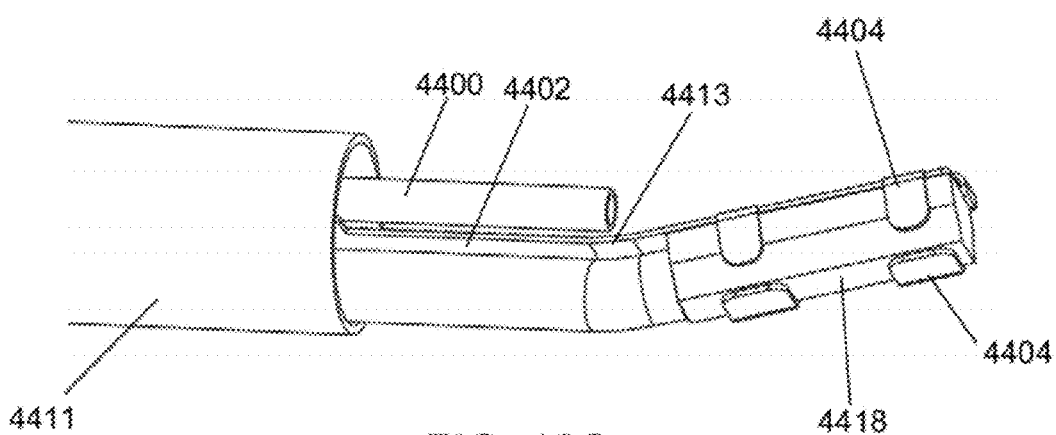
Figure 18D:
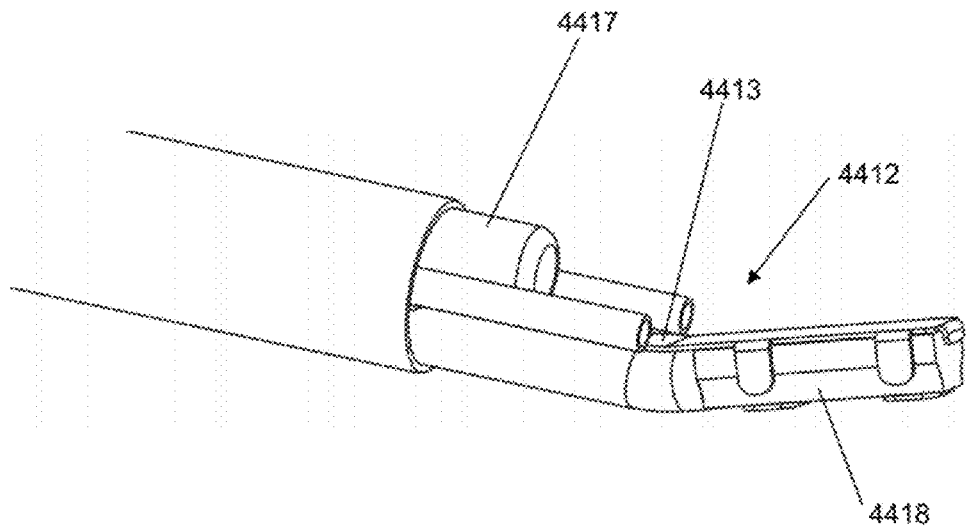
FIGS. 18D and 18E depict side perspective views of a mandrel that may be used with the endoscope retaining device of FIGS. 18A to 18C.
Figure 18E:
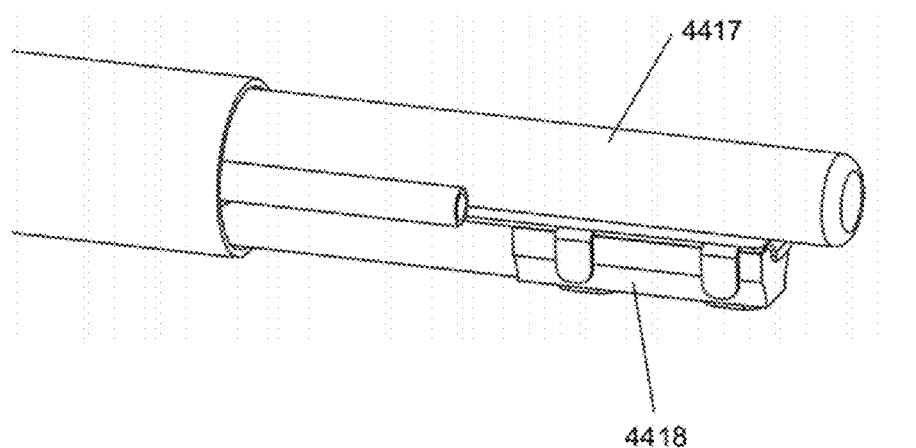
Figure 18F:
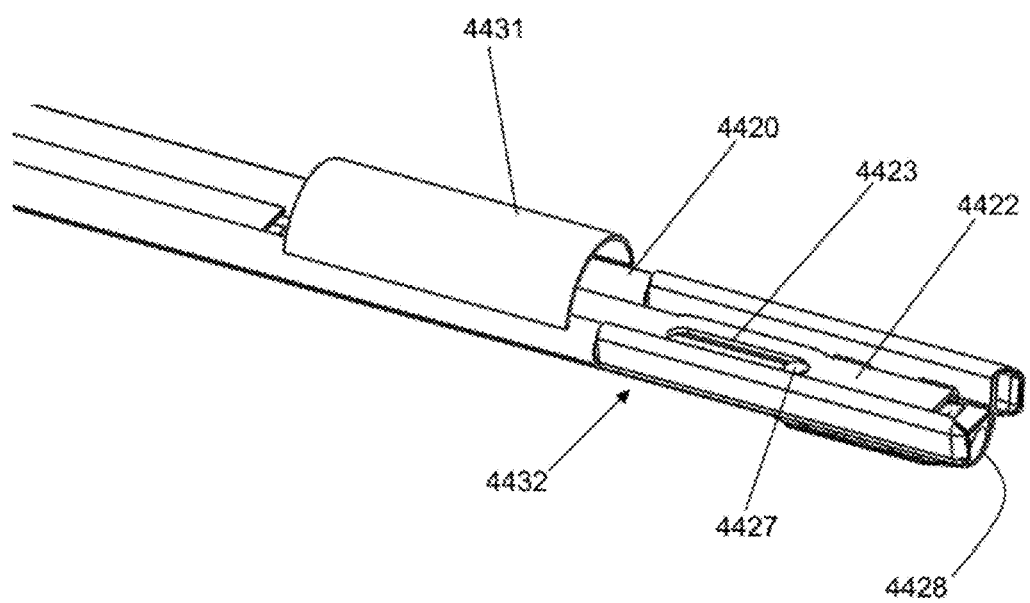
FIG. 18F is a superior elevational view of the support frame of the endoscope retaining device of FIGS. 18A to 18C.
Figure 18G:
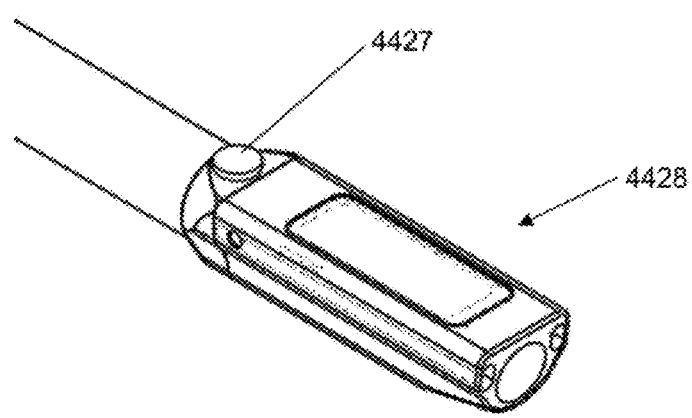
FIG. 18G is a superior elevational view of an exemplary endoscope that may be used with the endoscope retaining device of FIGS. 18A to 18C.
Figure 18H:
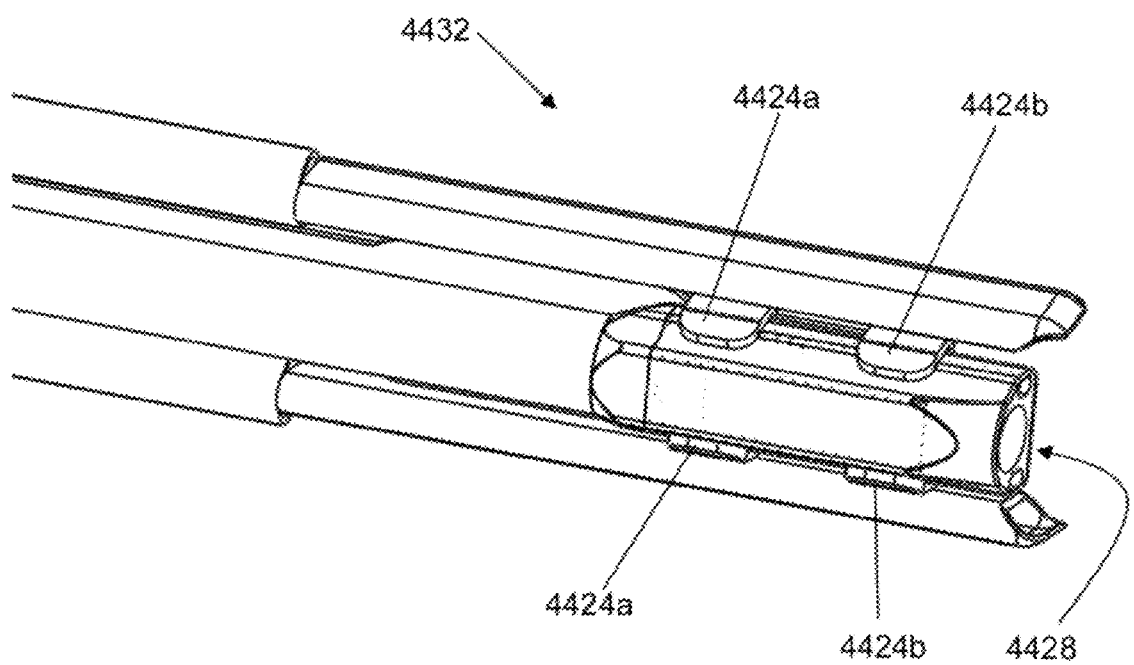
FIG. 18H is an inferior elevational view of the endoscope of FIG. 18G coupled to the endoscope retaining device of FIGS. 18A to 18C.

The distal portion of the base 4402 may be configured to retain an endoscope. For example, the distal portion of the base 4402 may comprise one or more retaining tabs 4404 that may be shaped to conform to an endoscope 4418. As illustrated in FIGS. 18B and 18C, some of the tabs 4404 may comprise a bend 4405 that may be configured to at least partially wrap around the endoscope 4418. The tabs 4404 may releasably engaged the endoscope 4418 by friction-fit, snap-fit, latch-fit, etc. The endoscope may comprise one or more grooves, slits, protrusions, notches, latches, etc. that may correspond to the tabs 4404 to help promote engagement with the support frame 4412. For example, the endoscope 4418 may comprise notches that may correspond with a hooked portion of a tab such that engagement between the slit and the tab hook act to couple the endoscope with the support frame. FIG. 18H depicts one variation where the support frame 4432 comprises a pair of proximal retaining tabs 4424a and a pair of distal retaining tabs 4424b that are configured to hold and/or stabilize the endoscope head. The endoscope 4428 may be inserted through the pair of proximal retaining tabs 4424a and advanced distally until engaged by both the proximal and distal retaining tabs. Alternatively or additionally, the endoscope 4418 and the support frame 4412 may each comprise magnetic components of opposite polarity, thereby coupling the endoscope to the support frame via magnetic forces. The magnetic components may be located at corresponding positions in the distal portion of the endoscope and support frame, and/or may be located at various positions along the length of the endoscope and support frame (e.g., one or more magnetic components at one or more locations along the length of the endo scope and support frame, magnetic components that extend continuously along the length of the endoscope and support frame, etc.).

In some variations, the base of a support frame may comprise a slot that corresponds to a protrusion on the endoscope. Insertion of the protrusion into the slot may help to axially align the endoscope with respect to the support frame. The slot may also define the length along which the endoscope may slide, and may axially provide a predetermined range of relative longitudinal movement between an endoscope and the support frame. FIG. 18F depicts one variation of a support frame 4432 comprising tubes 4420 coupled to a base 4422, where the base comprises a longitudinal slot 4423. FIG. 18G depicts one variation of an endoscope 4428 having a protrusion 4427 that may be configured to slidably engage with the slot 4423. The interaction between the protrusion 4427 and the slot 4423 may restrict the endoscope 4428 from sliding more distally than the distal-most wall of the slot 4427. This may help to ensure that after the endoscope is captured by retaining tabs 4424, the endoscope does not slide any further. The length and position of the slot 4423 with respect to the retaining tabs may be such that the endoscope cannot advance distally after it is captured by the retaining tabs, but proximal withdrawal of the endoscope along the length of the slot is sufficient to allow the endoscope to slide out of the retaining tabs. The protrusion 4427 may have any suitable shape (e.g., circular, rectangular, disc-like, etc.) and may be attached to the endoscope 4428 using any suitable means (e.g., laser-welding, adhesive-bonding, soldering, etc.).

A support frame may also comprise additional features that may help align and position the support frame within the lumen of a tubular member (e.g., the outer sheath, cannulotome shaft, introducer cannulae, etc.). In some variations, a support frame may comprise a protruding structure that displaces the tubular structures and base of the support frame to a desired location in the lumen. For example, as depicted in FIG. 18F, a support frame may comprise a protruding structure 4431 which may help to ensure that the support frame 4432 is centered and stabilized within a tubular member. The protruding structure 4431 may have a curvature that approximates the radius of curvature of the tubular member into which it is to be inserted. More generally, a protruding structure may have any size or shape to correspond with the tubular member. In some variations, the protruding structure may be an arched structure that extends along a longitudinal length of the support structure. The protruding structure 4431 may be integrally formed with the tubular structures 4420 or base 4422 of the support frame, or may be separated formed and attached to the support frame (e.g., by laser-welding, adhesive-bonding, soldering, etc.). The protruding structure 4431 may be located in the distal portion of the support frame 4432 or it may be located at any desired position along the length of the support frame (e.g., at a proximal portion, between the proximal and distal portion, center portion, etc.). While the support frame 4432 is depicted has having one protruding structure, other variations may comprise a plurality of protruding structures that may be located at various positions along the support frame.

While some support frames may be straight, other variations support frames may have a distal bend region. The bend region may direct an endoscope attached to the support frame at an angle with respect to the longitudinal axis of the device. This may enable the endoscope to acquire off-axis images. Referring back to FIGS. 18A-18C, the support frame 4412 may comprise a distal bend region 4413. The bend region 4413 may be made of the same or different material from the remainder of the support frame 4412. For example, the bend region 4413 may be made of a material that is more flexible than the remainder of the support frame, and may act as a living hinge to allow deflection of the distal tip. Alternatively, the bend region 4413 may be made of the same material as the remainder of the support frame, and may comprise regions of thinned material, thereby enabling deflection of the distal tip. In some variations, the bend region may have shape memory. The tubular structures 4400 may be attached to the base 4402 such that they do not extend distally beyond the bend region 4413, and in some cases, the attachment location 4415 of the tubular structures to the base may be proximal to the bend region 4413. This may allow for better flexion of the bend region 4413 (e.g., allow for a greater radius of curvature). In use, the bend region may transition between a stressed, straightened configuration and a relaxed, bent configuration. For example, as the support frame is advanced through the outer sheath, the bend region may have a straightened configuration, and may have a bent configuration after it exits the outer sheath. The bend region may have shape memory and have a bent rest position. While the support frame is restrained by the outer sheath, the bend region is straightened, but after it exits the sheath, it assumes its bent rest position. In other variations, the endoscope retaining device may comprise a straightening mandrel 4417, as depicted in FIGS. 18D and 18E. The mandrel 4417 may be longitudinally slidable along the length of the support frame, and in some variations, may be positioned between the two tubular structures 4400. The support frame 4412 may have a bent configuration when the distal end of the mandrel 4417 is located proximally to the bend region 4413 (FIG. 18D), and may have a straightened configuration when the distal end of the mandrel is located distally to the bend region (FIG. 18E). The mandrel 4417 may be used to control the bend configuration of the support frame 4412 regardless of the position of the distal portion of the support frame 4412 with respect to the outer sheath (e.g., the support frame may be in the bent configuration while in the outer sheath if the mandrel is proximal to the bend region).

Alternatively or additionally, the bend configuration of the support frame may be controlled by an endoscopic instrument (e.g., a rongeur, grasper, probe, dissector, etc.) with a relatively straight distal portion. The endoscopic instrument may be sized and shaped to extend along the support frame and/or between the tubular structures. When the endoscopic instrument is at a location that is proximal to the bend region, the support frame may be in the bent configuration where an endoscope coupled to the support frame may be directed to a field of view at an angle from the longitudinal axis of the endoscope retaining device (e.g., for off-axis viewing). When the endoscopic instrument is at a location that is distal to the bend region, the support frame may be in the straightened configuration, where the field of view is parallel to the longitudinal axis. This may be useful during a procedure, since the field of view would be parallel to and/or overlap with the working space of the endoscopic tool. For example, extending a grasper distal to the bend region may allow a practitioner to view the region of tissue that is accessible to the grasper. Having the endoscopic tool face in the same direction as the view angle of the endoscope may help the practitioner to navigate the endoscopic tool to the targeted tissue. Other mechanisms may be used to control the bend configuration of the support frame as appropriate, including mechanisms using pull cords, straightening rods, and the like.

Figure 19A:
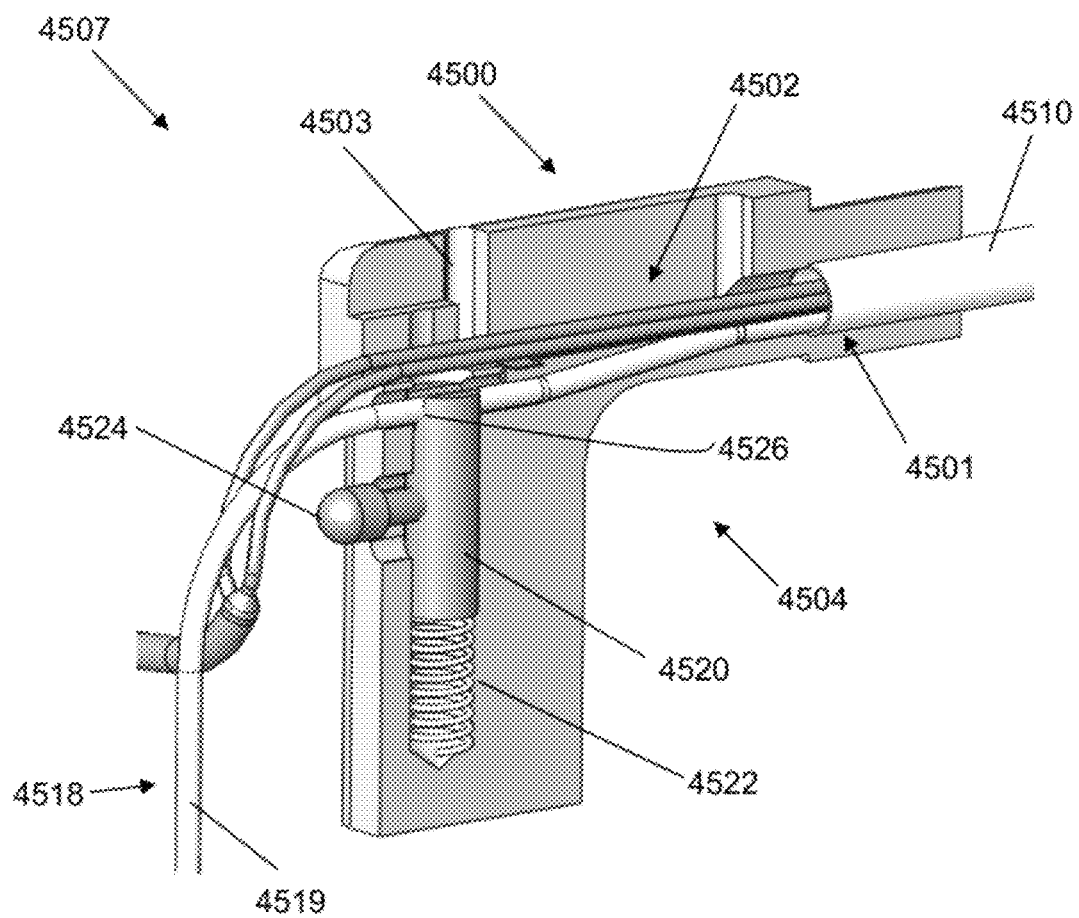
FIG. 19A depicts a partial cutaway of an exemplary endoscope retaining device.
Figure 19B:
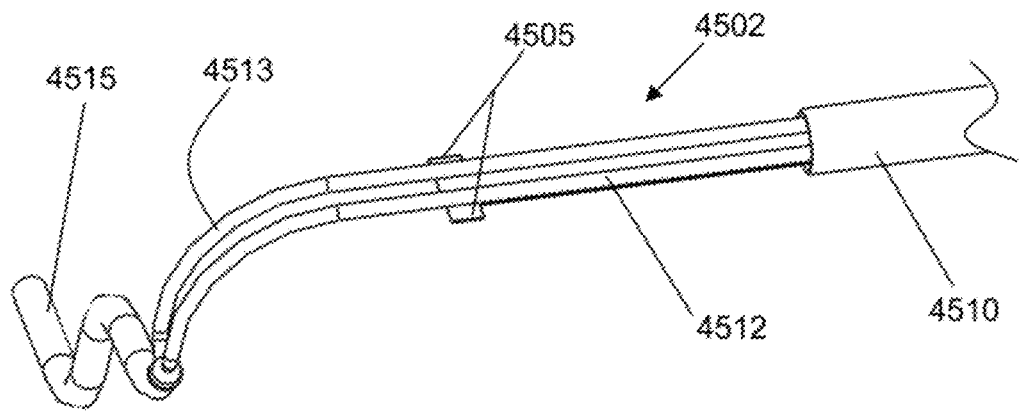
FIG. 19B depicts an elevational perspective component view of a portion of the support frame of the endoscope retaining device of FIG. 19A.
Figure 19C:
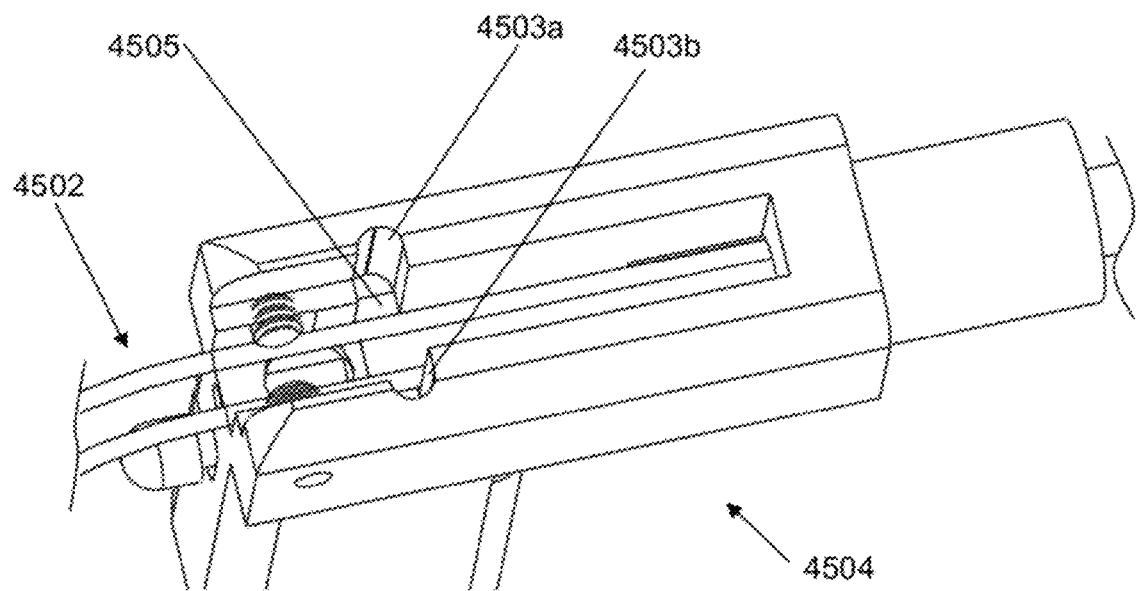
FIGS. 19C and 19D depict various perspective views of a proximal handle of the endoscope retaining device of FIG. 19A.
Figure 19D:
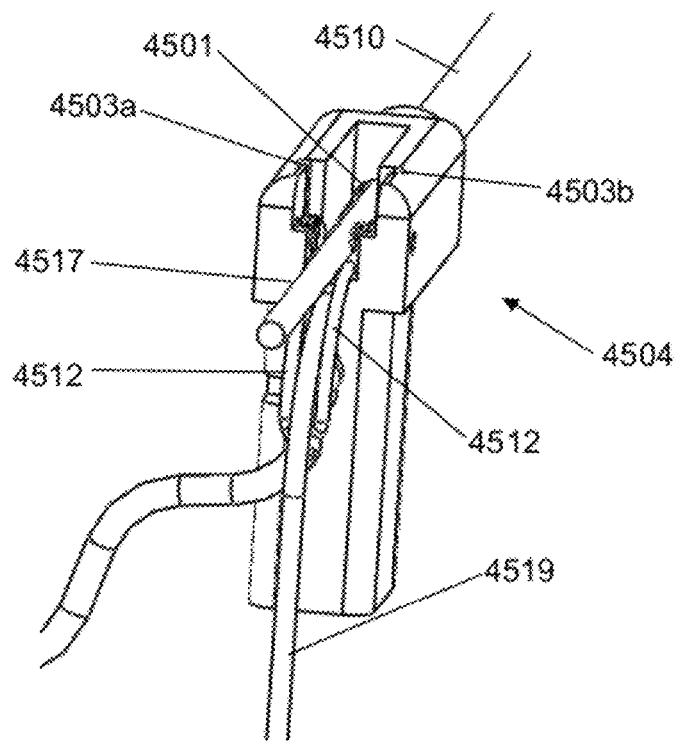
Figure 19E:
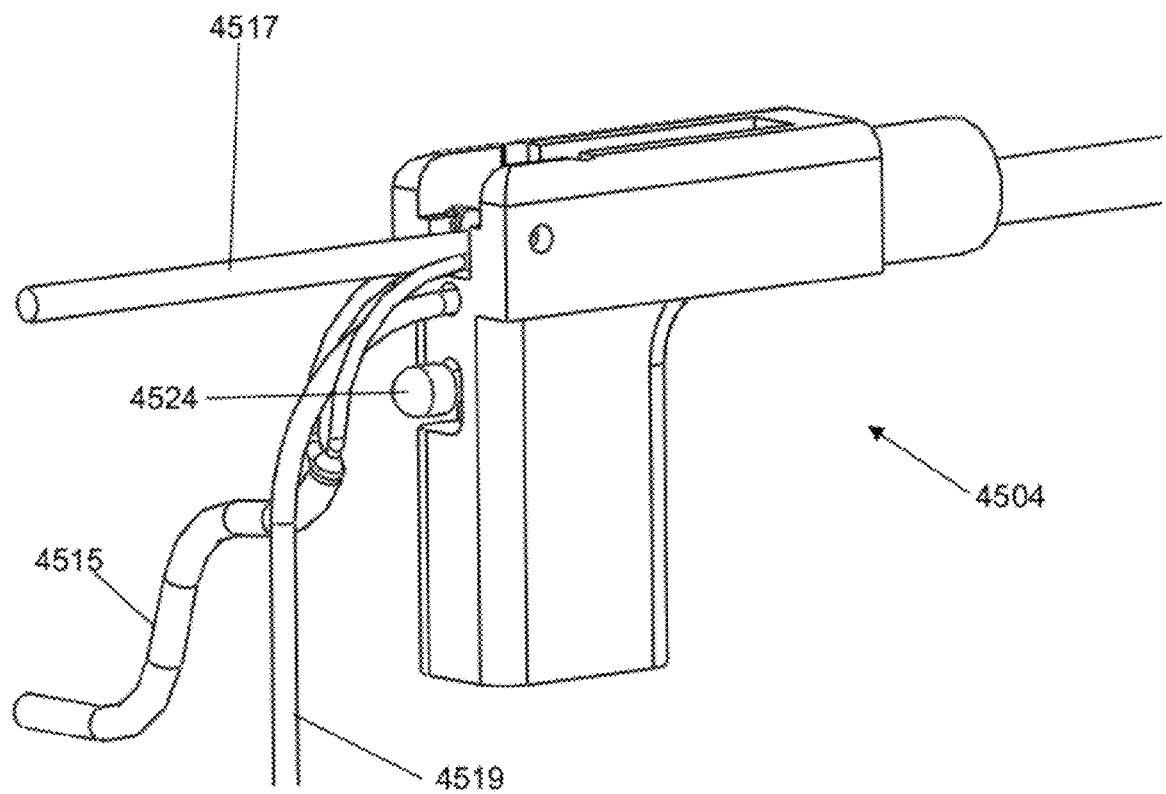
FIG. 19E depicts a side perspective view of the endoscope retaining device of FIG. 19A.

The support frame of an endoscope retaining device may be coupled to a proximal handle, as depicted in FIGS. 17B and 17C. FIGS. 19A-19C depict an endoscope assembly 4507 comprising an endoscope 4518 coupled to an endoscope retaining device 4500. These figures illustrate an example of how the endoscope retaining device support frame 4502 and the proximal handle 4504 may be coupled together. The handle 4504 may comprise one or more recesses 4503 that may correspond to one or more proximal tabs 4505 (FIG. 19B) of the support frame 4502 (e.g., the tabs may extend from the base of the support frame). As illustrated in FIG. 19C, the handle 4504 may comprise two recesses 4503a, 4503 that are configured to retain two proximal tabs 4505 of the support frame 4502 (the first proximal tab may be seen at the top of the figure, but the second proximal tab is obscured by the walls of the handle recess). The retention of the tabs 4505 within the recesses 4503 may help to axially fix the support frame to the handle and the outer sheath, and may prevent any axial rotation of the support frame, as well longitudinal movement with respect to the handle 4504. The handle 4504 may comprise additional recesses along the longitudinal length of the support frame to further stabilize and secure the position of the support frame with respect to the handle. The tubular structures 4512 of the support frame may be attached to the support frame base at or near the proximal tabs 4505. In some variations, a proximal portion 4513 of the tubular structures 4512 may be more flexible than a distal portion of the tubular structures. The rigid portion of the tubular structures may provide additional stiffness to the support frame, which may provide support to a flexible endoscope attached thereto, while the flexible portion of the tubular structures may facilitate the attachment of tubes (e.g., infusion tubes for flush solutions for irrigation, contrast solutions, etc.). The flexibility of the proximal portion 4513 may also allow the endoscope retaining device 4500 to be maneuvered and adjusted more readily as the device is used during a procedure. In some variations, the proximal portions 4513 of the support frame 4502 may be connected to a fluid reservoir via a fluid tube 4515, as illustrated in FIG. 19E. In other variations, each of the tubular structures may directly connect to a fluid reservoir, as may be desirable.

An outer sheath 4510 of the endoscope retaining device 4500 may be rigidly fixed to the handle 4504 by any suitable mechanism (e.g., laser-welding, adhesive-bonding, soldering, friction-fit, snap-fit, etc.). As depicted in FIGS. 19A and 19E, the outer sheath 4510 may be attached to a lumen 4501 of the handle 4504. In some variations, such as depicted in FIG. 19D, the support frame (e.g., the tubular structures 4512), endoscope cable 4519, and mandrel 4517 may extend through the lumen 4501 into the outer sheath 4510. In variations of endoscope retaining devices that do not have an outer sheath, the support frame, endoscope, and/or mandrel may extend through the handle via a similar lumen.

An endoscope may be coupled to an endoscope retaining device using a variety of mechanisms. For example, an endoscope may be coupled to an attachment tab, which is then coupled to the endoscope retaining device, as described above and illustrated in FIG. 17B. Endoscopes may also be coupled to an endoscope retaining device via one or more latches, set screws, magnets, etc. Alternatively or additionally, an endoscope cable 4519 of the endoscope 4518 may be secured to the proximal handle 4504 by a block 4520 mounted to a spring 4522 as depicted in FIG. 19A. The block 4520 may comprise a notch 4526 that is sized and shaped to engage and/or retain the endoscope cable 4519. The block 4520 may be coupled to a button 4524 that may be used to pull the block 4520 up or down. For example, the spring 4522 may bias the block 4520 to an up position, which may capture and secure the endoscope cable 4519 within the notch 4526. As depicted in FIG. 19E, the block 4520 may press up against an internal wall 4523 of the handle 4504, which may secure the endoscope cable 4519 by compressing it within the notch 4526. To release the endoscope cable 4519, the button 4524 may be slid downward against the spring force, thereby allowing the cable to slide through the notch 4526. While the notch 4526 is depicted with a V-shaped geometry, it should be understood that the notch may have any size and shape such that an endoscope cable may be slidably retained therein.

Figure 19F:
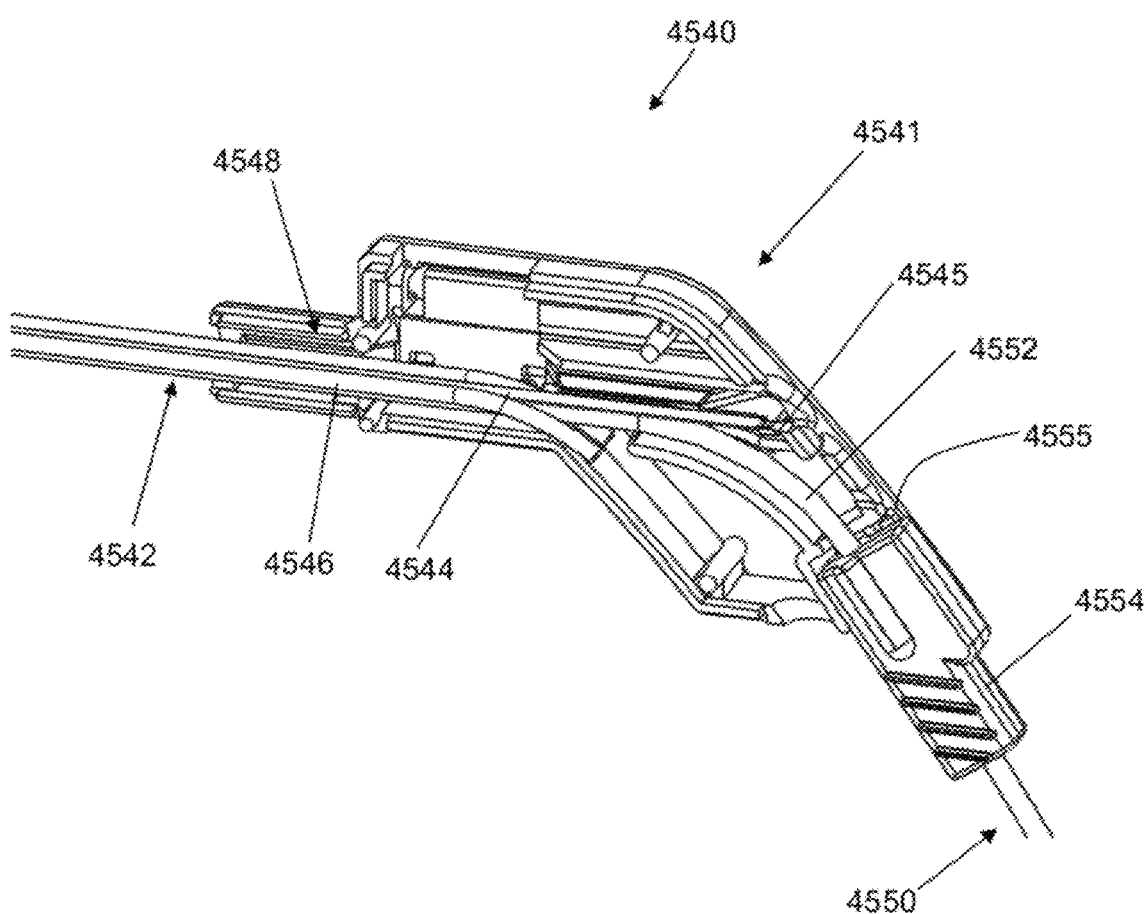
FIG. 19F depicts a perspective partial cutaway view of a handle portion of another exemplary endoscope retaining device.

FIG. 19F depicts a partial cutaway of another variation of a proximal handle 4541 of an endoscope retaining device 4540 that retains an endoscope without the use of a spring mechanism. As illustrated there, a support frame 4542 comprising a base 4544 and two tubular structures 4546 attached along the length of the base, where the support frame is attached to the proximal handle 4541 via proximal tabs 4545. The proximal ends of the tubular structures 4546 may be connected to one or more fluid tubes (which is not shown in FIG. 19F) that may be in communication with a fluid reservoir. The support frame 4542 extends distally through a lumen 4548. The endoscope retaining device 4540 may optionally comprise an outer sheath that may connect with the handle 4541 via the lumen 4548. Endoscope 4550 may comprise a cable 4552 that may be releasably coupled to an attachment tab 4554 that in turns couples the endoscope to the endoscope retaining device. For example, the attachment tab 4554 may be made of an elastomeric material and sized to fit within an opening 4555 of the proximal handle, where the dimensions of the opening prevent the attachment tab from moving or shifting after it is installed.

Figure 20A:
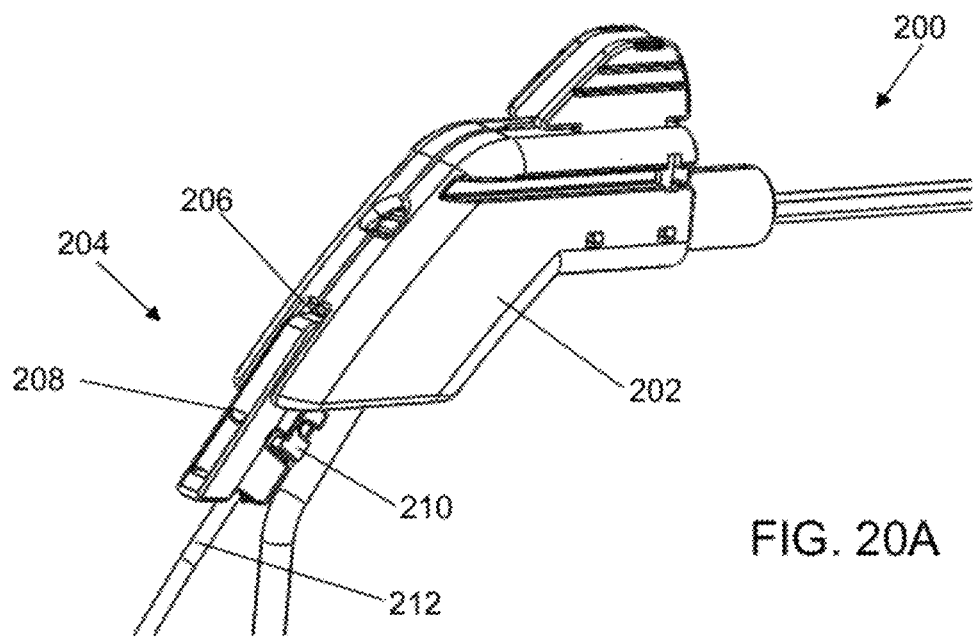
FIG. 20A is a side perspective view of an exemplary endoscope retaining device having a latch mechanism for retaining an endoscope.
Figure 20B:
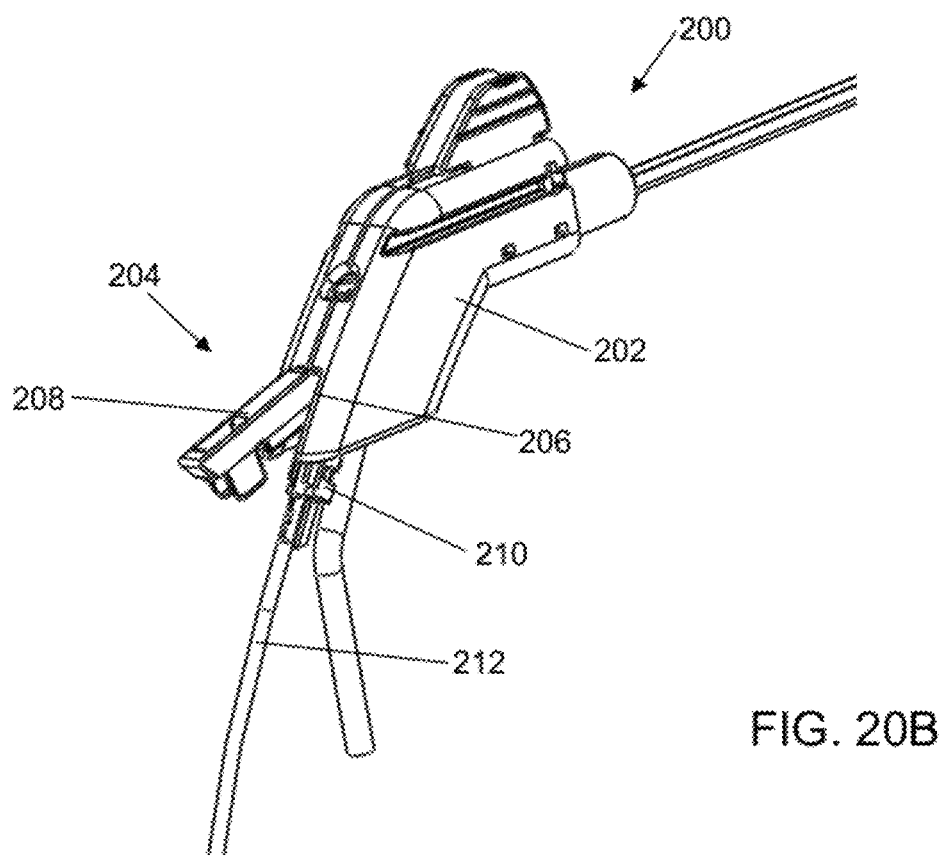
FIG. 20B depicts the endoscope retaining device of FIG. 20A where the latch mechanism is in an unlocked configuration.
Figure 20C:
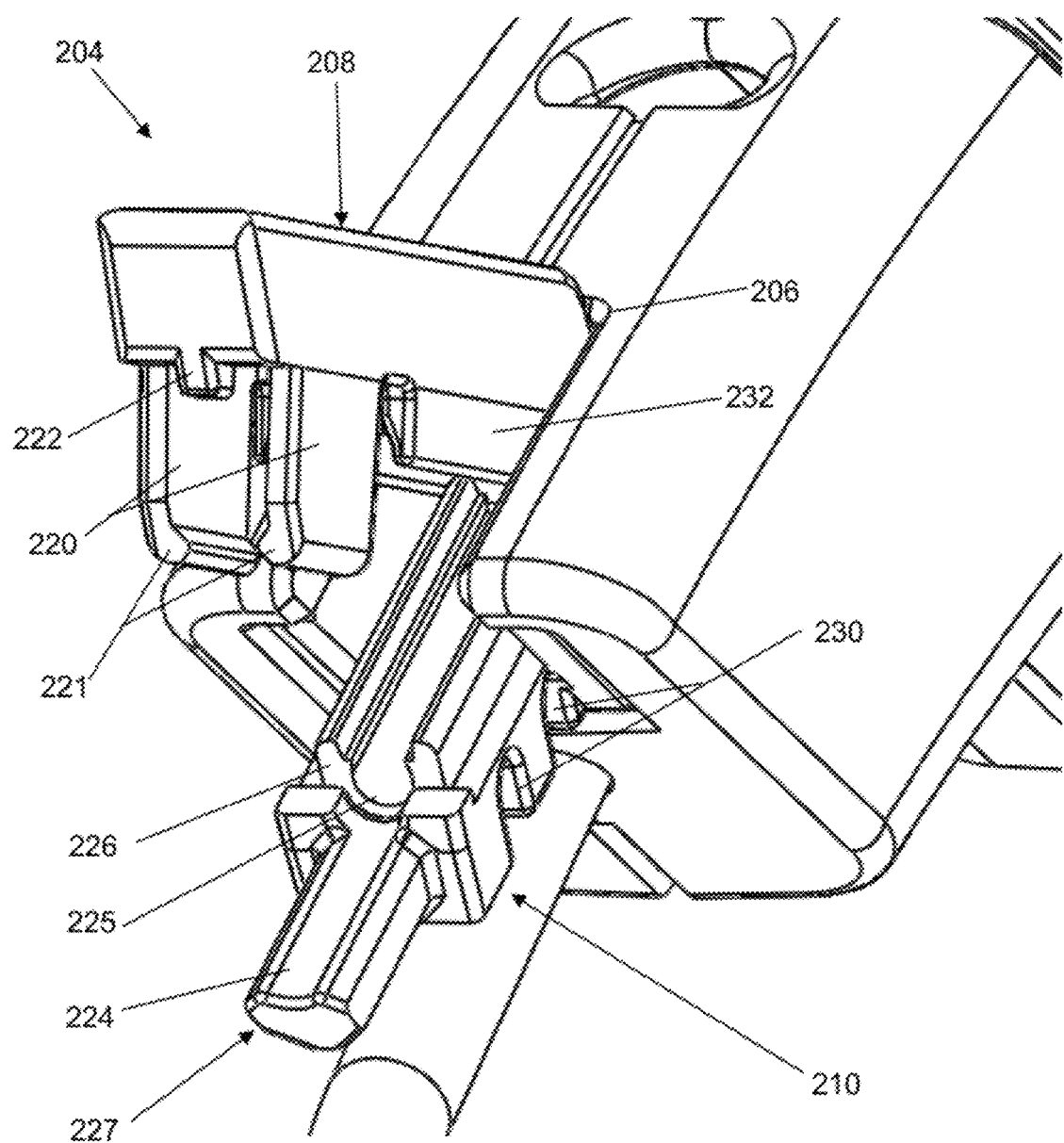
FIGS. 20C and 20D are close-up perspective views of the latch mechanism (without an endoscope) of the endoscope retaining device of FIG. 20A.
Figure 20D:
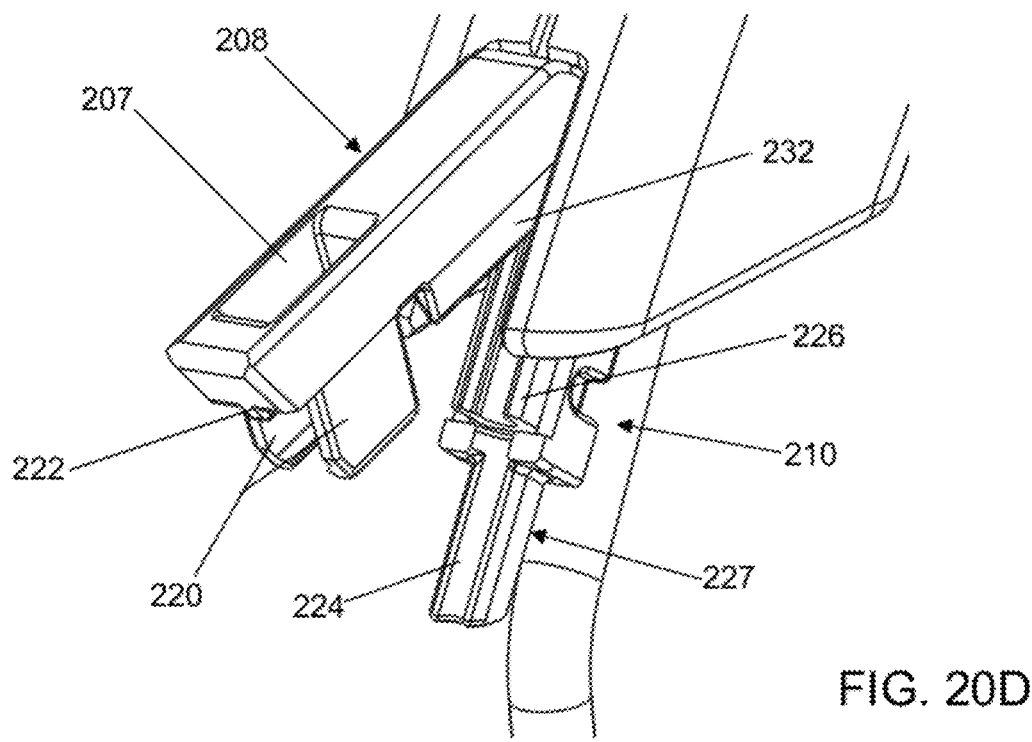

Additionally or alternatively, an endoscope cable (e.g., of a flexible endoscope or a fiberscope) may be attached to the proximal handle of an endoscope retaining device using a latch-based mechanism. The endoscope may be attached such that it is axially aligned along a support structure of the endoscope retaining device. FIGS. 20A-20E depict one example of an endoscope retaining device 200 that uses a latch mechanism to releasably secure an endoscope cable. As depicted in FIG. 20A, the endoscope retaining device 200 may comprise a proximal handle 202 having a latch mechanism 204 that may be used to secure an endoscope cable 212 (e.g., the shaft of a fiberscope). The latch mechanism 204 may comprise a pivotable bar 208 and a stationary bar 210, where the pivotable bar and the stationary bar fit within a slot 206 in the proximal handle 202. The pivotable bar 208 may be configured to rotate around a hinge (not shown) to transition the latch mechanism between a locked configuration (where the endoscope cable 212 is secured within the handle) and an unlocked configuration (where the endoscope cable 212 is releasable from the handle). FIG. 20A depicts the locked configuration, where the pivotable bar 208 is within the slot 206 such that the pivotable bar 208 is within the slot 206 and engaged with the stationary bar 210. FIG. 20B depicts the unlocked configuration, where the pivotable bar 208 is at least partially displaced from the slot 206 and disengaged from the stationary bar 210. In the unlocked configuration, the endoscope cable 212 may be released from the proximal handle 202 (e.g., by sliding proximally along the longitudinal axis of the cable). The endoscope cable 212 may be clamped and secured between the pivotable bar 208 and the stationary bar 210. FIGS. 20C and 20D depict the latch mechanism 204 of endoscope retaining device 200 in detail. The stationary bar 210 may be fixedly located within the slot 206. The stationary bar 210 may have a channel for retaining an endoscope cable, where the channel is communication with a lumen of the endoscope retaining device that contains the support frame. This may allow an endoscope retained by the latch mechanism 204 to contact and align with the support frame, as previously described. The endoscope cable channel may be formed by a series of longitudinal grooves. For example, the stationary bar 210 may comprise an elongate groove 224 on a proximal protrusion 227. The channel 225 between the walls of the cable rail 226 and the elongate groove 224 may not be aligned along the same plane; that is, an endoscope cable extending from the elongate groove 224 may "step up" to the cable rail 226. The cable rail 226 may be made of an elastomeric material, such that compression of the cable rail by the pivotable bar 208 may compress the endoscope cable, thereby securing it in place. Examples of suitable elastomeric materials may include silicone, urethane, and the like. The stationary bar 210 may also comprise one or more notches 230 on either side of the bar, where the notches may be configured engage a portion of the elastomeric cable rail 226 (e.g., to attach the cable rail to the rest of the stationary bar 210).

The pivotable bar 208 may comprise one or more tabs that may be used to engage with the stationary bar 210. For example, the pivotable bar 208 may comprise a pair of side tabs 232 located along each side of the pivotable bar 208. The length and location of the side tabs 232 may correspond to the length and location of the cable rail 226 of the stationary bar 210. In the locked configuration, these side tabs 232 may compress the walls of the cable rail 226 inward, which may provide a compressive force on an endoscope cable within the rail channel 225. The increased compressive force may provide frictional resistance to longitudinal sliding of the endoscope cable and thereby secure the endoscope cable. The pivotable bar 208 may also comprise a pair of proximal side tabs 220 with deflectable tips 221 that are curved inward. The location of the side tabs 220 along the pivotable bar 208 may correspond to the protruding portion of the stationary bar 210 with the elongate groove 224. In the locked configuration, the proximal side tabs 220 may engage with the stationary bar 210 by a snap-lock interaction with the protrusion 227, where the curved tips 221 deflect around and snap onto the protrusion 227. This engagement between the side tabs 220 and the protrusion 227 may act to keep the pivotable bar 208 within the slot 206 to secure an endoscope within the endoscope retaining device. The pivatoble bar 208 may also comprise an end tab 222 located at a proximal-most surface of the pivotable bar 208. In the locked configuration, the end tab 222 may provide additional compressive force to the endoscope cable. While a latch mechanism has been described herein, it should be understood that the endoscope may be releasably engaged with the handle of the endoscope retaining device using one or more mechanisms, including magnetic engagement, any suitable clamp mechanisms (e.g., rotatable clamps, spring-based clamps, etc.), and the like.

Figure 20E:
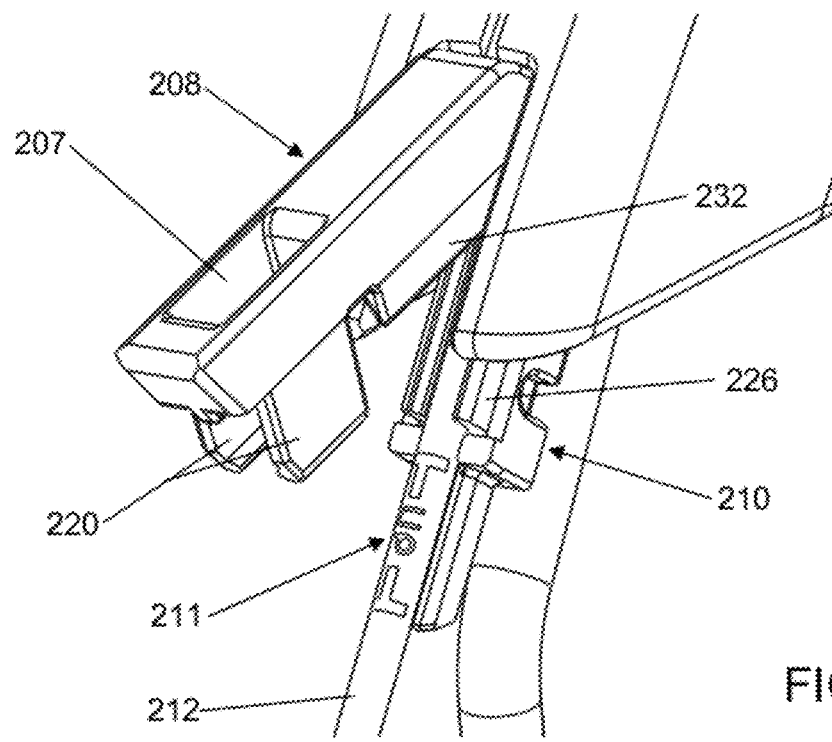
FIG. 20E is a close-up perspective view of the latch mechanism (with an endoscope) of the endoscope retaining device of FIG. 20A.

FIG. 20E depicts the latch mechanism of an endoscope retaining device in an unlocked configuration with an endoscope cable. As depicted there, the endoscope cable 212 may comprise one more orientation indicator 211 that may help ensure that the endoscope is installed in a known orientation. In some variations, the orientation indicator 211 may be an installation instruction to indicate which surface of the endoscope cable should be facing up. The pivotable bar 208 may also comprise an aperture 207 such that the orientation indicator 211 is visible even when the latch is in the locked configuration. This may allow a practitioner to confirm the orientation of the endoscope throughout the procedure, in the event that mechanical manipulation (e.g., tapping, torquing, etc.) of the endoscope retaining device and/or cannulotome caused the endoscope to rotate or otherwise change its position.

Figure 21A:
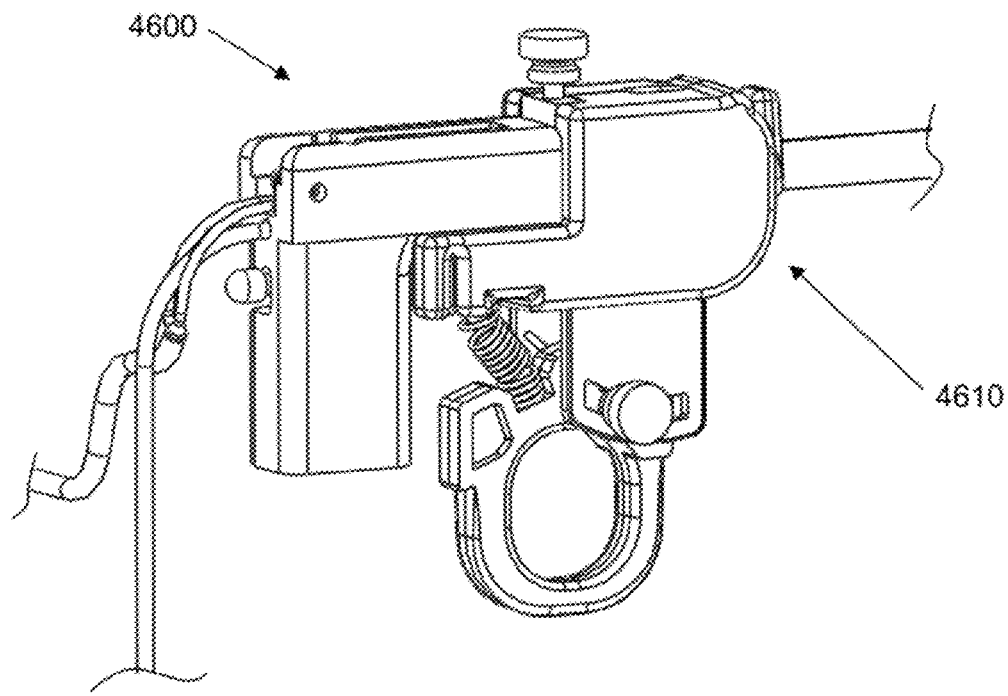
FIG. 21A is a perspective view of an exemplary endoscope retaining device coupled to a cannula device.
Figure 21B:
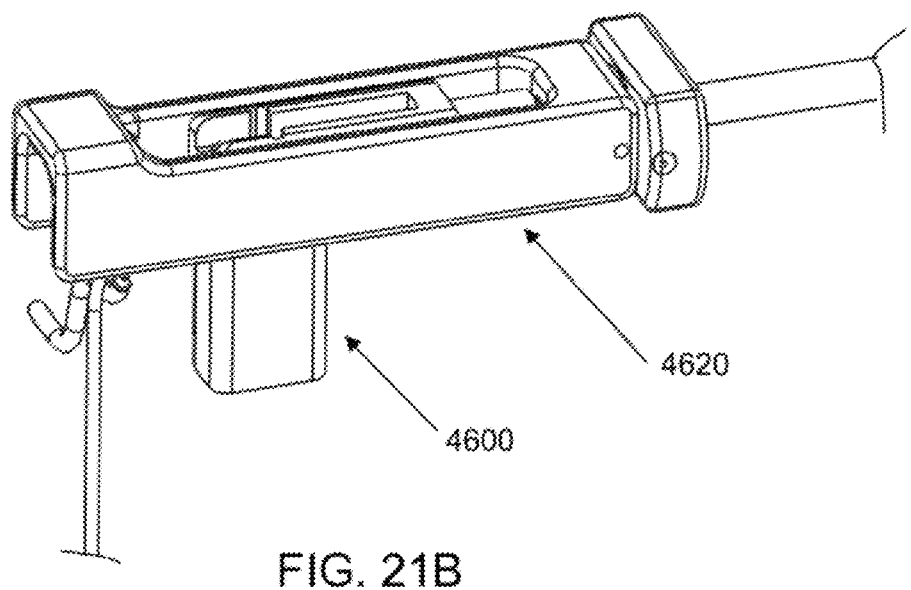
FIG. 21B is a perspective view of an exemplary endoscope retaining device coupled to one example of a cannulotome.

The endoscope retaining devices described herein may be configured to be assembled with a variety of tools that may be used during a procedure to treat spinal stenosis. For example, an endoscope assembly 4600 comprising an endoscope coupled to an endoscope retaining device may be configured to releasably couple to a cannula device 4610 (FIG. 21A). In some variations, the endoscope assembly 4600 may also be configured to releasably couple to a retractor cannula assembly. Endoscope assembly 4600 may also be configured to releasably couple to a cannulotome 4620 (FIG. 21B). Compatibility of the endoscope retaining device 4600 with a variety of devices may enable endoscopic visualization at one or more stages of a spinal stenosis procedure. For example, images may be acquired when the spinal region is first accessed by an introducer cannula, before or during the removal of tissue by the cannulotome, and/or may be used to identify the location of the target tissue and tissue regions that are to be avoided. In some variations, an endoscope coupled to an endoscope retaining device may be advanced through an introducer cannula to confirm the location of a target tissue site, after which it may be withdrawn from the introducer cannula. A cannulotome may then be advanced through the introducer cannula to contact the target tissue. The endoscope coupled to the endoscope retaining device may be advanced through the shaft of the cannulotome throughout the procedure to image and/or monitor the progress of tissue removal.

Cannulotomes as described herein may be used to remove tissue using shaving or chiseling motions. For example, the sharpened distal edge of a cannulotome may be rotated (e.g., about the longitudinal axis of the length of the cannulotome), and/or translated laterally (e.g., along the longitudinal axis of the cannulotome), or any combination of such movements. In some procedures, tissue may be removed by rotating the cannulotome about 30° to about 180° while laterally contacting the tissue along the longitudinal axis of the cannulotome.

One method of treating stenosis using one or more of the devices described previously may comprise advancing a k-wire into area near a facet (or alternatively disc at a posterolateral trajectory, e.g., 30-90 degrees from the sagittal plane). A dilator with a cannula may be placed over the k-wire. The cannula used for this and other procedures described herein may include simple tubular cannulae, as well as cannulae having additional viewing structures and/or tissue protective structures, such as the cannulae described in U.S. patent application Ser. No. 12/582,638 filed on Oct. 20, 2009, which has already been incorporated by reference herein in its entirety. The dilator may then be removed. An endoscope with a working channel may be inserted in the cannula. Rongeurs/probes may be inserted through the working channel and used to expose and identify nerve and stenotic tissue. The endoscope and tools may be removed from the cannula. The endoscope may then be inserted inside of a cannulotome, and the endoscope-cannulotome assembly may be inserted into the cannula, and advanced to the target stenosis site. Under direct visualization, the cannulotome may be rotated so that the cutter, e.g., a wedge-shaped cutter, of the cannulotome may engage the stenotic tissue to be removed, while preserving the adjacent nerve. A mallet may be used to tap or strike the proximal ledge of the cannulotome to drive the cutter into stenotic tissue, while in other variations, the device may be configured with a motor to facilitate a jack-hammer like action. The wedge-shaped cutter may pry the cut tissue (bone/ligament) away from its attachment as it is advanced distally. The cannulotome may then be rotated to sweep a larger arc as necessary to cut out larger sector of the stenotic tissue. The cannulotome may then be pulled back to disengage the tissue. A rongeur may then be inserted through the endoscope's working channel to grasp the cut tissue and remove it from the tissue site. For foraminal stenosis, the target tissue to be removed may be around the intervertebral foramen. To treat central stenosis, the tissue removal procedure as described above may be used to open up the foramen to allow for the cannula, cannulotome, and endoscope to be advanced deeper and into the central canal to further remove stenotic tissue therein.

Another variation of a method of treating stenosis using one or more of the devices described previously may comprise attaching an endoscope to an endoscope retaining device (i.e., an endoscope assembly). The endoscope assembly may then be inserted into a cannulotome. The position of the endoscope assembly within the cannulotome may be adjusted to attain the desired field of view. Then, the endoscope assembly may be engaged to the cannulotome by a spring-based friction-fit to stabilize visualization with the endoscope during the procedure. The cannulotome, coupled with the endoscope assembly, may be inserted into an introducer cannula. The introducer cannula may then be advanced to the target tissue site. The target tissue site may be imaged with the endoscope (using any suitable imaging method, e.g., fluoroscopic imaging methods, etc.) to help position the distal cutter of the cannulotome against the bone targeted for removal. Optionally, the distal tip of the endoscope assembly may be deflected by retracting a straightening mandrel and/or endoscopic tool (e.g., a rongeur, grasper, probe, dissector, etc.), which may further adjust the field of view. A proximal end of the cannulotome may be tapped with a mallet in order to remove the targeted bone. Bone removal may take place under direct endoscopic visualization (e.g., images may be acquired using the endoscope while the cannulotome is tapped). Additional images may be acquired as the cannulotome contacts the bone to ensure that the cutter is contacting the targeted bone. Markings on the inner surface of the distal cutter may be used to facilitate with the placement of the cutter with respect to the target tissue site. The cannulotome may be rotated (e.g., using a rotation knob on the proximal handle) to re-position it at the tissue site, as well as to help free the targeted one fragment by fracturing bone. Rotation of the cannulotome may also cut soft tissue, for example, by engaging tissue with a notch on the cutter. The cutter may also have a roughened and/or textured surface that may be used to grind and/or shave bone or soft tissue, which may help loosen it for removal. The cannulotome may be re-positioned by retracting the cannulotome within the introducer cannula, rotated within the cannula while the cannula is repositioned at the targeted tissue site, and then advanced through the cannula to contact additional targeted bone. Once the targeted bone has been fractured and detached, a grasping device may be advanced to the tissue site to remove the bone fragments. The grasping device may be advanced through the introducer cannula, a working lumen within the endoscope, or a lumen of the cannulotome. These steps may be repeated as necessary until the desired target tissue has been removed.

A method for treating herniation may comprise removing tissue to open up the intervertebral foramen as described above. The cannulotome and endoscope may be advanced through the foramen into the epidural space or central canal and rongeurs can be used to remove herniated discs. In some variations, the cannulotome may be advanced into the epidural space independent of the cannula, while in other variations, the cannula and cannulotome may be generally advanced together into the epidural space. In still other variations, the cannulotome may be removed from the body once a sufficient passage through the foramen is created or achieved, while leaving other tools or components in place to facilitate treatment or visualization of the epidural space.

A method for treating degenerative disc may comprise removing tissue to open up the intervertebral foramen as described above. The cannulotome and endoscope may be advanced through the foramen into the disc and rongeurs can be used to remove disc material so that a fusion cage can be inserted into the disc through the cannula.

One or more of the cannulotome described herein may be used to perform laminectomy as well for interlaminar approach. In one example of the method, a dilator may be advanced to the lamina using posterior anterior trajectory. A cannula may be slid over the dilator down to the lamina. An endoscope may then be inserted inside of a cannulotome, and the assembly may be inserted into the cannula and advanced to the lamina. Under direct visualization, the cannuoltome may be rotated so that the distal cutter, e.g., a wedge-shaped cutter, may engage the lamina section to be removed. A mallet may be used to tap the proximal ledge on the cannulotome to drive the wedge-shaped cutter into lamina. The wedge-shaped cutter may pry the cut tissue (bone/ligament) away from its attachment as it advances distally. The cannulotome may then be rotated to sweep a larger arc as necessary to cut out larger sector of the connective tissue around the lamina such as ligamentum flavum. The cannulotome may then be pulled back to disengage the tissue. A rongeur may then be inserted through the working channel of the endoscope to grasp and remove the cut tissue. In this way a channel may be created into the epidural space. The dilator with the cannula may then be advanced distally into the epidural space. The dilator may then be removed. The access path to the epidural space may facilitate the removal of disc and stenotic tissue surrounding the epidural space to help decompress nerve.

Kits comprising devices for the treatment of stenosis may comprise an introducer cannula, an endoscope, an endoscope retaining device, and a cannulotome. Some kits may additionally comprise one or more cannulotomes that have distal cutters with various sizes and shapes and introducer cannulae with various diameters. In some variations, a kit may also comprise one or more devices that may be used to remove tissue, such as a rongeur, a reamer, a rasp, or a curette. A kit may also comprise cannula devices configured for dissecting and retracting tissue, as well as devices for facilitating access to a target tissue region. Examples access devices that may be included in a kit may include a deflectable cannula, a stylet (typically 16-19G), an exchange wire, and a dilator. A kit may also comprise instructions for using each of these devices.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The invention claimed is:

1. A system, comprising:
    a tissue removal device including:
        a handle; and
        an elongate shaft having a longitudinal axis, and a lumen terminating at a distal opening, the distal opening including a perimeter with a rigid tapered protrusion, wherein the rigid tapered protrusion comprises a proximal base and a distal cutting edge, at least one-quarter of the perimeter of the distal opening being at or proximal to the base, and a proximal edge of the distal opening forms the border of a plane that is transverse to and intersected by a longitudinal axis of the elongate shaft; and
    an endoscope assembly including:
        a flexible endoscope; and
        an endoscope retaining device including an elongate support structure configured to receive the flexible endoscope, the endoscope retaining device being configured to be inserted into the lumen of the elongate member of the tissue removal device and coupled to the handle of the tissue removal device in a predetermined radial orientation, such that when the endoscope assembly is inserted into the lumen of the elongate shaft of the tissue removal device a proximal-most portion of the endoscope retaining device is distal to a proximal-most portion of the handle of the tissue removal device.

2. The system of claim 1, wherein the cutting edge comprises a notch, wherein a proximal-most portion of the notch is distal to the plane.

3. The system of claim 2, wherein the tapered protrusion comprises an exterior surface and an interior surface that converge at the distal cutting edge of the rigid tapered protrusion, an angle between the exterior and interior surfaces being equal to or greater than 5° and equal to or less than 10°.

4. The system of claim 3, wherein the exterior surface of the tapered protrusion includes one or more recesses configured to retain a therapeutic substance therein.

5. The system of claim 4, wherein each of the one or more recesses have either a circular shape or a rectangular shape.

6. The system of claim 3, wherein the interior surface of the tapered protrusion comprises one or more markings.

7. The system of claim 6, wherein each of the one or more markings comprises one or more lines parallel to the longitudinal axis of the elongate shaft.

8. The system of claim 1, further comprising a cannula, wherein the tissue removal device is configured to extend through the cannula.

9. The system of claim 1, wherein the endoscope retaining device further comprises a proximal handle including a latch mechanism configured to retain a cable of the endoscope.

10. The system of claim 9, wherein the latch mechanism comprises a pivotable bar and a stationary bar, the stationary bar configured to fit within a slot in the proximal handle and comprising a cable rail configured to retain the endoscope cable.

11. The system of claim 10, wherein the latch mechanism has a first unlocked configuration wherein the endoscope cable may be released from the stationary bar, and a second locked configuration wherein the endoscope cable is retained within the stationary bar.

12. The system of claim 11, wherein in the second locked configuration, one or more tabs of the pivotable bar engage with a portion of the stationary bar, such that a compressive force retains the endoscope cable within the stationary bar.

13. The system of claim 12, wherein the stationary bar comprises an elastomeric cable rail configured to retain the endoscope cable therethrough, and wherein in the second locked configuration, the one or more tabs of the pivotable bar engage and compress the elastomeric cable rail such that compressive forces retain the endoscope cable within the cable rail.

14. The system of claim 13, wherein the endoscope cable comprises one or more orientation indicators and wherein the pivotable bar comprises an aperture in a location that corresponds to the location of the orientation indicators when the endoscope cable is retained within the endoscope retaining device.

15. The system of claim 9, wherein the proximal handle is attached to a proximal portion of the elongate support structure, and wherein the elongate support structure comprises a distal securing element configured to partially enclose a distal circumferential surface of the endoscope in a predetermined rotational alignment, while partially exposing the distal circumferential surface of the endoscope.

16. The system of claim 15, wherein a distal securing structure comprises one or more retention tabs configured to engage the distal portion of an endoscope.

17. The system of claim 15, wherein the elongate support structure comprises one or more tubular channels configured to transport fluid along the support structure, wherein each tubular channel comprises an external surface and an internal surface.

18. The system of claim 15, wherein support structure comprises a longitudinal slot configured to axially provide a predetermined range of relative longitudinal movement between an endoscope and the support structure.

19. The system of claim 15, wherein a distal portion of the support structure comprises a bend region, wherein the bend region has a first relaxed bent configuration and second stressed straight configuration.

20. The system of claim 19, further comprising a mandrel insertable through the endoscope retaining device and along the support structure, wherein in the first straight configuration, the mandrel is in a position distal to the bend region, and in the second bent configuration, the mandrel is in a position proximal to the bend region.

21. The system of claim 19, further comprising a grasper tool insertable through the endoscope retaining device and along the support structure.

22. The device of claim 1, wherein the elongate shaft has a length from about 2 inches to about 8 inches.

\* \* \* \* \*